United States Patent
Hikita

(10) Patent No.: US 10,085,615 B2
(45) Date of Patent: Oct. 2, 2018

(54) ENDOSCOPE APPARATUS, IMAGE PROCESSING APPARATUS AND IMAGE ADJUSTING METHOD

(71) Applicant: FUJIFILM Corporation, Tokyo (JP)

(72) Inventor: Mai Hikita, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 658 days.

(21) Appl. No.: 14/681,925

(22) Filed: Apr. 8, 2015

(65) Prior Publication Data

US 2015/0312483 A1    Oct. 29, 2015

(30) Foreign Application Priority Data

Apr. 23, 2014   (JP) ................. 2014-089114

(51) Int. Cl.
| | |
|---|---|
| A61B 1/00 | (2006.01) |
| A61B 1/05 | (2006.01) |
| H04N 5/77 | (2006.01) |
| G06T 3/40 | (2006.01) |
| H04N 5/262 | (2006.01) |
| H04N 5/357 | (2011.01) |
| H04N 5/345 | (2011.01) |
| H04N 5/225 | (2006.01) |

(52) U.S. Cl.
CPC ........ *A61B 1/0002* (2013.01); *A61B 1/00009* (2013.01); *A61B 1/00045* (2013.01); *A61B 1/05* (2013.01); *G06T 3/40* (2013.01); *H04N 5/2628* (2013.01); *H04N 5/3454* (2013.01); *H04N 5/3572* (2013.01); *H04N 5/77* (2013.01); *H04N 2005/2255* (2013.01)

(58) Field of Classification Search
CPC ....................................... G06T 3/40

USPC ............................. 348/65; 382/283; 600/109
See application file for complete search history.

(56) References Cited

U.S. PATENT DOCUMENTS

| | | | | |
|---|---|---|---|---|
| 2005/0073578 A1* | 4/2005 | Odlivak | ............... | G06F 19/322 348/65 |
| 2010/0048993 A1* | 2/2010 | Shidara | .............. | A61B 1/00057 600/109 |

FOREIGN PATENT DOCUMENTS

| | | |
|---|---|---|
| JP | 2008-253789 A | 10/2008 |
| JP | 4772826 B2 | 9/2011 |

* cited by examiner

*Primary Examiner* — Alexandra L Newton
*Assistant Examiner* — Rynae Boler
(74) *Attorney, Agent, or Firm* — Birch, Stewart, Kolasch & Birch, LLP

(57) ABSTRACT

An endoscope apparatus includes an observation optical system, a solid-state imaging element, a memory section, and an image processing section, wherein the memory section stores the information therein for specifying the image cutting-out region for the process of cutting out the image for display, which corresponds to an overlapping region in which a displayable pixel area of the solid-state imaging element and an imaging area of the optical image to be formed on the solid-state imaging element by the observation optical system overlap one another, and overlap one another when the center of the imaging area is matched with the center of the display area, as the image cutting-out information, and the image processing section expands the image for display to an image size of the display area, when an image size of the cut-out image for display becomes smaller than the image size of the display area.

9 Claims, 20 Drawing Sheets

ENDOSCOPE APPARATUS, IMAGE PROCESSING APPARATUS AND IMAGE ADJUSTING METHOD

CROSS-REFERENCE TO RELATED APPLICATIONS

The patent application claims priority under 35 U.S.C. § 119 to Japanese Patent Application No. 2014-89114, filed on Apr. 23, 2014. Each of the above application(s) is hereby expressly incorporated by reference, in its entirety, into the present application.

BACKGROUND OF THE INVENTION

Field of the Invention

The present invention relates to an endoscope apparatus which has an observation optical system and a solid-state imaging element; an image processing apparatus which subjects an image that has been obtained by this endoscope apparatus to image processing, and outputs the processed image to a monitor; and an image adjusting method for the endoscope apparatus.

Description of the Related Art

Conventionally, medical diagnosis using an electronic endoscope is conducted in a medical field. The electronic endoscope which is referred to as a scope, for instance, is provided with an insertion section which is inserted into the body of a patient. In an inner space of a tip portion of the insertion section, which is the tip site of the insertion section, there are provided an observation optical system, a solid-state imaging element that images an optical image which is formed by the observation optical system, and the like.

The solid-state imaging element is attached to and fixed in a solid-state imaging element frame in the tip portion of the insertion section, or is fixed in a shield frame by a sealing resin, and accordingly accuracy of an attachment position of the solid-state imaging element occasionally becomes low. In addition, the accuracy of an attachment position of the observation optical system in the tip portion of the insertion section also becomes occasionally low, similar to that of the solid-state imaging element. In such a case, it becomes difficult to match the center of an effective pixel area 300 of the solid-state imaging element with the center of an imaging area 302 of the observation optical system as shown in FIG. 19. In addition, a part of the effective pixel area 300 is used in image processing, and accordingly it does not always occur that the center of the effective pixel area 300 matches with the center of a display area 304 of an image displayed on the monitor as shown in FIG. 19. For this reason, a defect such as an angle of deviation occurs in the image displayed on the monitor.

Then, an imaging apparatus described in Japanese Patent No. 4772826 is structured to make the center of the observation optical system (imaging area) match with the center of the display area, and thereby obtain an adequate image having no defect therein such as the angle of deviation.

SUMMARY OF THE INVENTION

However, there is the case where a margin of an effective pixel area with respect to an imaging area of an observation optical system, and a margin of the imaging area with respect to a display area each cannot be allocated, along with a recent tendency of miniaturization of an observation optical system and a solid-state imaging element of an electronic endoscope. In such a case, when the attachment accuracy of the solid-state imaging element and the like is low, even though the center of the imaging area is matched with the center of the display area as described in the above described Japanese Patent No. 4772826, there is a possibility that a part (portion displayed by hatching in the figure) of a region in which an imaging area 302 and a display area 304 overlap one another is positioned in the outside of an effective pixel area 300, as shown in FIG. 20. As a result, a part of an optical image corresponding to the display area 304 results in being formed in the outside of the effective pixel area, and thereby vignetting occurs in an image displayed on the monitor.

The present invention is designed with respect to such a circumstance, and an object of the invention is to provide an endoscope apparatus, an image processing apparatus and an image adjusting method for the endoscope apparatus, which can obtained an adequate image that shows no vignetting, even when attachment accuracy of a solid-state imaging element and an observation optical system is low.

An endoscope apparatus for attaining an object of the present invention includes: an observation optical system; a solid-state imaging element that is relatively positioned and fixed with respect to the observation optical system, obtains an optical image formed thereon by the observation optical system, and has a plurality of photoelectric conversion elements arrayed therein which photoelectrically convert the optical image; a memory section that stores image cutting-out information therein that specifies an image cutting-out region for a process of cutting out an image for display, which corresponds to a display area to be displayed on a monitor, from an image generated on the basis of an imaging signal of the solid-state imaging element; and an image processing section which cuts out the image for display from the image, on the basis of the image cutting-out information stored in the memory section, wherein the memory section stores the information therein for specifying the image cutting-out region for the process of cutting out the image for display, which corresponds to an overlapping region in which a displayable pixel area of the solid-state imaging element and an imaging area of the optical image to be formed on the solid-state imaging element by the observation optical system overlap one another, and overlap one another when the center of the imaging area is matched with the center of the display area, as image cutting-out information, and the image processing section expands the image for display to an image size of the display area, when an image size of the cut-out image for display becomes smaller than the image size of the display area due to deviation between the center of the displayable pixel area and the center of the imaging area.

According to the present invention, the image for display, which has been expanded to the image size of the display area can be displayed on the monitor, even when a part of a region in which the imaging area and the display area overlap one another is positioned in the outside of the displayable pixel area, due to low attachment accuracy of the solid-state imaging element and the observation optical system.

In the endoscope apparatus according to another aspect of the present invention, the memory section further stores magnification information therein which shows the magnification for a process of expanding the image for display to the image size of the display area, and the image processing section expands the image for display according to the magnification information which is stored in the memory section. The image for display can be easily adjusted to the image size of the display area, by only expanding the image for display, which has been cut out according to the magnification information that has been previously stored in the memory section.

In the endoscope apparatus according to another aspect of the present invention, the memory section has image cutting-out information and magnification information corresponding to each of a plurality of display areas stored therein, and is provided with a selecting section which selects the display area to be displayed on the monitor out of the plurality of display areas, and the image processing section acquires the image cutting-out information and the magnification information corresponding to the display area which has been selected in the selecting section from the memory section, cuts out the image for display from the image on the basis of the image cutting-out information, and expands the image for display according to the magnification information. Thereby, an adequate observation image which shows no vignetting can be obtained, even when the display area is selected and switched to another one.

In the endoscope apparatus according to another aspect of the present invention, the image cutting-out information which is stored in the memory section is information which shows the image cutting-out region having the same aspect ratio as that of the display area. Thereby, an image free from a feeling of strangeness can be displayed on the monitor, even when the image for display has been expanded.

In the endoscope apparatus according to another aspect of the present invention, in the case where the numbers of pixels in a vertical direction and a horizontal direction in the displayable pixel area are represented by 2V and 2H, the numbers of pixels in a vertical direction and a horizontal direction in the display area are represented by $2L_V$ and $2L_H$, and amounts of deviation between the center of the displayable pixel area and the center of the imaging area in a vertical direction and a horizontal direction in terms of the numbers of pixels are represented by $D_V$ and $D_H$, the image processing section expands the image for display, when the image cutting-out information is information that shows the image cutting-out region in which at least either of the following Expression (1) and Expression (2) is satisfied. Thereby, it can be prevented that the image cutting-out process and the image expanding process are carried out even when there is no need for these processes to be conducted.

$$V - L_V \leq D_V \qquad (1)$$

$$H - L_H \leq D_H \qquad (2)$$

In the endoscope apparatus according to another aspect of the present invention, when magnification in which the image for display is expanded is represented by m, the image processing section expands the image for display at a higher magnification out of the magnifications m expressed by the following Expression (3) and Expression (4), respectively. Thereby, the image size of the cut-out image for display can be expanded to the image size of the display area.

$$m = L_V / (V - D_V) \qquad (3)$$

$$m = L_H / (H - D_H) \qquad (4)$$

In the endoscope apparatus according to another aspect of the present invention, when the higher magnification is admissible magnification or less, the image processing section expands the image for display. Thereby, an observation image of poor image quality can be prevented from being displayed.

In the endoscope apparatus according to another aspect of the present invention, the image for display is subjected to a masking process of masking the image for display so as to become the same shape as that of the display area, by the image processing section. Thereby, the image for display having the same shape as that of the display area can be displayed on the monitor.

An image processing apparatus for attaining an object of the present invention is an image processing apparatus that generates an image for display, which corresponds to a display area to be displayed on a monitor, from an image generated on the basis of an imaging signal of a solid-state imaging element that is relatively positioned and fixed with respect to an observation optical system, obtains an optical image formed thereon by the observation optical system, and has a plurality of photoelectric conversion elements arrayed therein which photoelectrically convert the optical image, and outputs the image for display to the monitor, furthermore, includes: an information acquiring section which acquires image cutting-out information from a memory section that stores image cutting-out information therein that specifies an image cutting-out region for a process of cutting out the image for display from the image; and an image processing section which cuts out the image for display from the image on the basis of the image cutting-out information that the information acquiring section has acquired, wherein the information acquiring section acquires information for specifying the image cutting-out region for a process of cutting out the image for display, which corresponds to an overlapping region in which a displayable pixel area of the solid-state imaging element and an imaging area of the optical image to be formed on the solid-state imaging element by the observation optical system overlap one another, and overlap one another when the center of the imaging area is matched with the center of the display area, as the image cutting-out information, from the memory section, and the image processing section expands the image for display to an image size of the display area, when an image size of the cut-out image for display becomes smaller than the image size of the display area due to deviation between the center of the displayable pixel area and the center of the imaging area.

An image adjusting method for an endoscope apparatus for attaining an object of the present invention, includes: a storing step of making a memory section store image cutting-out information that specifies an image cutting-out region for a process of cutting out an image for display, which corresponds to a display area to be displayed on a monitor, from an image generated on the basis of an imaging signal of a solid-state imaging element that is relatively positioned and fixed with respect to an observation optical system, obtains an optical image formed thereon by the observation optical system, and has a plurality of photoelectric conversion elements arrayed therein which photoelectrically convert the optical image; and an image processing step of cutting out the image for display from the image on the basis of the image cutting-out information stored in the memory section, wherein in the storing step, the memory section stores information for specifying the image cutting-out region for a process of cutting out the image for display, which corresponds to an overlapping region in which a displayable pixel area of the solid-state imaging element and an imaging area of the optical image to be formed on the solid-state imaging element by the observation optical system overlap one another, and overlap one another when the center of the imaging area is matched with the center of the display area, as the image cutting-out information, and in the image processing step, the image processing section expands the image for display to an image size of the display area, when an image size of the cut-out image for display becomes smaller than the image size of the display area due to deviation between the center of the displayable pixel area and the center of the imaging area.

In the image adjusting method for the endoscope apparatus according to another aspect of the present invention, in the storing step, the memory section further stores magnification information showing magnification for a process of expanding the image for display to the image size of the display area, and in the image processing step, the image for display is expanded according to the magnification information which is stored in the memory section.

The endoscope apparatus, the image processing apparatus and the image adjusting method for the endoscope apparatus in the present invention can obtain an adequate image which shows no vignetting even when attachment accuracy of a solid-state imaging element and an observation optical system is low.

DETAILED DESCRIPTION OF THE PREFERRED EMBODIMENTS

An endoscope apparatus according to the present invention will be described below with reference to the attached drawings.

[Overall Structure of Endoscope Apparatus]

Figure 1:
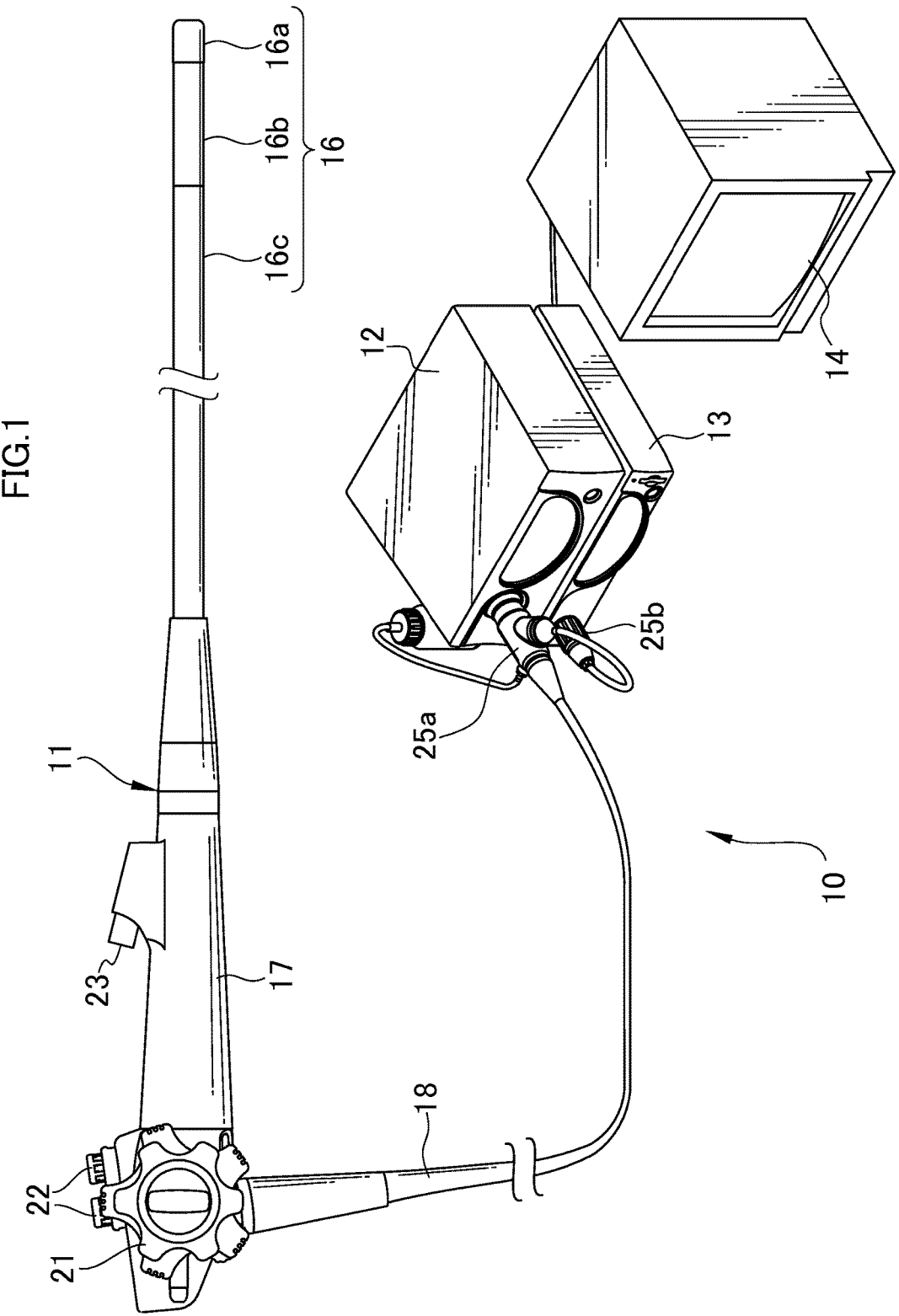
FIG. 1 is a perspective view of an endoscope apparatus according to the present invention.

FIG. 1 is a perspective view of an appearance of an endoscope apparatus (hereinafter referred to as endoscope system as well) 10 according to the present invention. The endoscope apparatus 10 has, if being roughly divided, an electronic endoscope 11 that functions as a scope (hereinafter referred to as flexible endoscope) through which a site to be observed in a patient body is imaged; a light source device 12; a processor device 13; a monitor 14; and the like.

The light source device 12 supplies illuminating light which illuminates the site to be observed, to the electronic endoscope 11. The processor device 13 is a device corresponding to one form of the image processing apparatus of the present invention; and generates image data for an image for display (hereinafter referred to as image data for display) which is displayed on the monitor 14 on the basis of an imaging signal that is obtained by the electronic endoscope 11, and outputs the generated image data to the monitor 14. The monitor 14 displays the observation image of the site to be observed on the basis of the image data which is input from the processor device 13.

The electronic endoscope 11 includes: a flexible insertion section 16 which is inserted into the patient body; an operating section 17 which is continuously provided in the base end of the insertion section 16, and is used for grasping the electronic endoscope 11 and operating the insertion section 16; and a universal cord 18 which connects the operating section 17 to the light source device 12 and the processor device 13.

A tip portion 16a of the insertion section, which is a tip site of the insertion section 16, contains an observation optical system that is used in illumination and photographing of the site to be observed, a solid-state imaging element, and the like therein. In the rear end of the tip portion 16a of the insertion section, a curving portion 16b which can be freely curved is continuously provided. In addition, in the rear end of the curving portion 16b, a flexible pipe portion 16c having flexibility is continuously provided.

The operating section 17 has an angle knob 21, operation buttons 22, a forceps inlet 23 and the like provided therein.

When the curving direction and the curving quantity of the curving portion 16b are adjusted, the angle knob 21 is rotationally operated. The operation buttons 22 are used in various operations such as air feeding/water feeding and suction. The forceps inlet 23 communicates with a forceps channel in the insertion section 16.

The universal cord 18 has an air feeding/water feeding channel, a signal cable, a light guide and the like incorporated therein. A connector portion 25a which is connected to the light source device 12, and a connector portion 25b which is connected to the processor device 13 are provided in the tip portion of the universal cord 18. Thereby, the illuminating light is supplied from the light source device 12 to the electronic endoscope 11 through the connector portion 25a, and also the imaging signal which has been obtained by the electronic endoscope 11 is input into the processor device 13 through the connector portion 25b.

[Electrical Configuration of Endoscope Apparatus]

Figure 2:
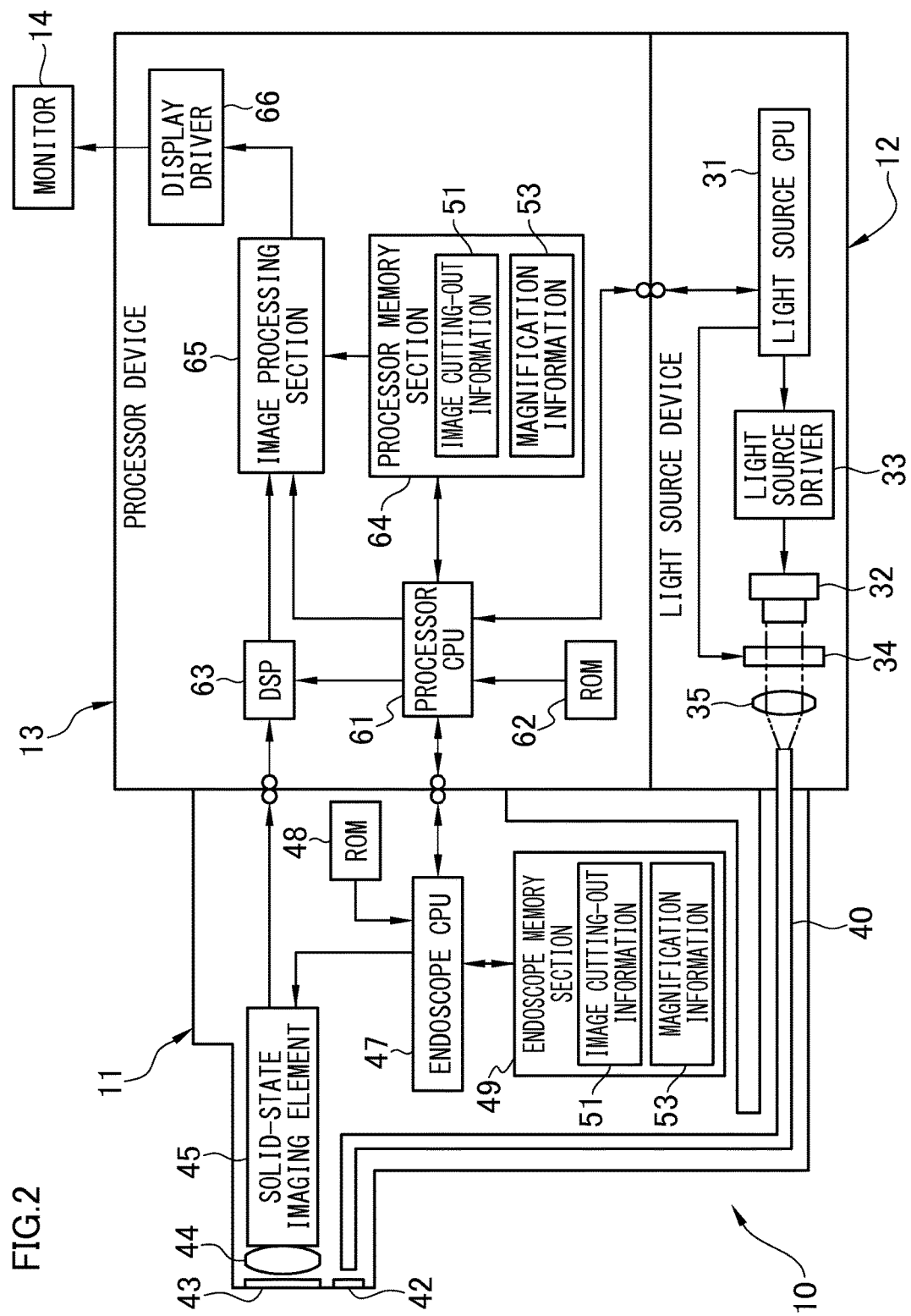
FIG. 2 is a block diagram showing an electrical configuration of the endoscope apparatus.

FIG. 2 is a block diagram showing an electrical configuration of the endoscope apparatus 10. As shown in FIG. 2, a light source device 12 has a light source CPU (Central Processing Unit) 31, a light source 32, a light source driver 33, a diaphragm mechanism 34 and a condensing lens 35. The light source CPU 31 controls the light source driver 33 and the diaphragm mechanism 34. In addition, the light source CPU 31 communicates with a processor CPU 61 in the processor device 13, and exchanges various information one another.

A semiconductor light source such as an LED (Light Emitting Diode) and an LD (Laser Diode), a xenon lamp or the like is used as the light source 32, and the light source driver 33 controls an outgoing beam of illuminating light. The diaphragm mechanism 34 is arranged in the light outgoing side of the light source 32, and increases and decreases the quantity of the illuminating light which is emitted from the light source 32 and incident on the condensing lens 35. The condensing lens 35 condenses the illuminating light which has passed through the diaphragm mechanism 34, and guides the condensed light to an incident end of a light guide 40, in the connector portion 25a which is connected to the light source device 12.

The electronic endoscope 11 has, if being roughly divided, the light guide 40, an illumination window 42, an observation window 43, an observation optical system 44, a solid-state imaging element 45, an endoscope CPU 47, a ROM (Read Only Memory) 48 and an endoscope memory section 49.

An optical fiber having a large diameter, a bundle fiber and the like are used as the light guide 40. As for the light guide 40, the incident end thereof is inserted into the light source device 12 through the connector portion 25a, and the outgoing end thereof faces the illumination window 42 provided in the tip portion 16a of the insertion section, after having passed through the insertion section 16. The illuminating light which has been supplied to the light guide 40 from the light source device 12 is irradiated the site to be observed through the illumination window 42. The illuminating light which has been reflected/scattered on the site to be observed is incident on the observation optical system 44 through the observation window 43.

The observation optical system 44 is arranged in the back side of the observation window 43. The observation optical system 44 forms an optical image of the site to be observed, which is specifically reflected light or scattered light of the illuminating light, which has been incident through the observation window 43, on the imaging plane of the solid-state imaging element 45.

The solid-state imaging element 45 is a CMOS (complementary metal oxide semiconductor) type imaging element or a CCD (charge coupled device) type imaging element, and is relatively positioned and fixed to the observation optical system 44 at a position in a more back side than the observation optical system 44. A plurality of pixels are two-dimensionally arrayed on the imaging plane of the solid-state imaging element 45, which are formed of a plurality of photoelectric conversion elements PD (Photo Diode) (see FIG. 3) each of which photoelectrically converts the optical image. The solid-state imaging element 45 converts the optical image which is formed by the observation optical system 44 into an electrical imaging signal, and outputs the converted signal to the processor device 13.

When the solid-state imaging element 45 is the CMOS type imaging element, the solid-state imaging element 45 contains an A/D converter therein and outputs a digital imaging signal directly to the processor device 13. In addition, when the solid-state imaging element 45 is the CCD type imaging element, the imaging signal which is output from the solid-state imaging element 45 is converted into a digital imaging signal by an unillustrated A/D converter or the like, and then the converted signal is output to the processor device 13.

The endoscope CPU 47 sequentially carries out various programs and data which have been read out from the ROM 48 and the like, and mainly controls the driving of the solid-state imaging element 45. When the solid-state imaging element 45 is the CMOS type imaging element, the endoscope CPU 47 may be contained in the solid-state imaging element 45.

In addition, the endoscope CPU 47 communicates with the processor CPU 61 in the processor device 13, and transmits information which is stored in the ROM 48 and the endoscope memory section 49, to the processor device 13. The ROM 48 stores, for instance, identification information for identifying the type of the electronic endoscope 11 therein, as information to be transmitted to the processor device 13.

The endoscope memory section 49 corresponds to one form of the memory section of the present invention. The endoscope memory section 49 previously stores image cutting-out information 51 and magnification information 53 therein which will be described later in detail, as the information to be transmitted to the processor device 13, when the electronic endoscope 11 is manufactured.

The processor device 13 has the processor CPU 61, a ROM 62, a digital signal processing circuit (DSP: Digital Signal Processor) 63, a processor memory section 64, an image processing section 65, and a display driver 66.

The processor CPU 61 reads out necessary program and data from the ROM 62, sequentially processes the program and data, and thereby controls each section in the processor device 13. In addition, the processor CPU 61 outputs the identification information which has been transmitted from the endoscope CPU 47, to the DSP 63, and outputs the image cutting-out information 51 and the magnification information 53 to the image processing section 65. Accordingly, the processor CPU 61 corresponds to one form of an information acquiring section of the present invention.

The DSP 63 subjects an image signal for one frame, which has been input from the electronic endoscope 11, to various signal processes such as color interpolation, color separation, color balance adjustment, gamma correction and image enhancement processing, under the control of the processor CPU 61, and generates image data for one frame. Incidentally, the DSP 63 conducts various signal processes according to the type (model) of the electronic endoscope 11, on the basis of the identification information which has been input from the processor CPU 61. In addition, the DSP 63 sequentially outputs the generated image data for every one frame to the image processing section 65.

The processor memory section 64 is a section which corresponds to one form of the memory section of the present invention. The processor memory section 64 stores the image cutting-out information 51 and the magnification information 53 therein which have been input from the processor CPU 61.

The image processing section 65 subjects the image data which is input from the DSP 63 on the basis of the image cutting-out information 51 and the magnification information 53 that have been acquired from the processor memory section 64, to image cutting-out process, image expanding process and masking process, under the control of the processor CPU 61, and generates image data for display. Then, the image processing section 65 outputs the image data for display to the display driver 66.

The display driver 66 makes the monitor 14 display the observation image of the site to be observed, on the basis of the image data for display, which is input from the image processing section 65.

[Image Cutting-Out Information]

Figure 3:
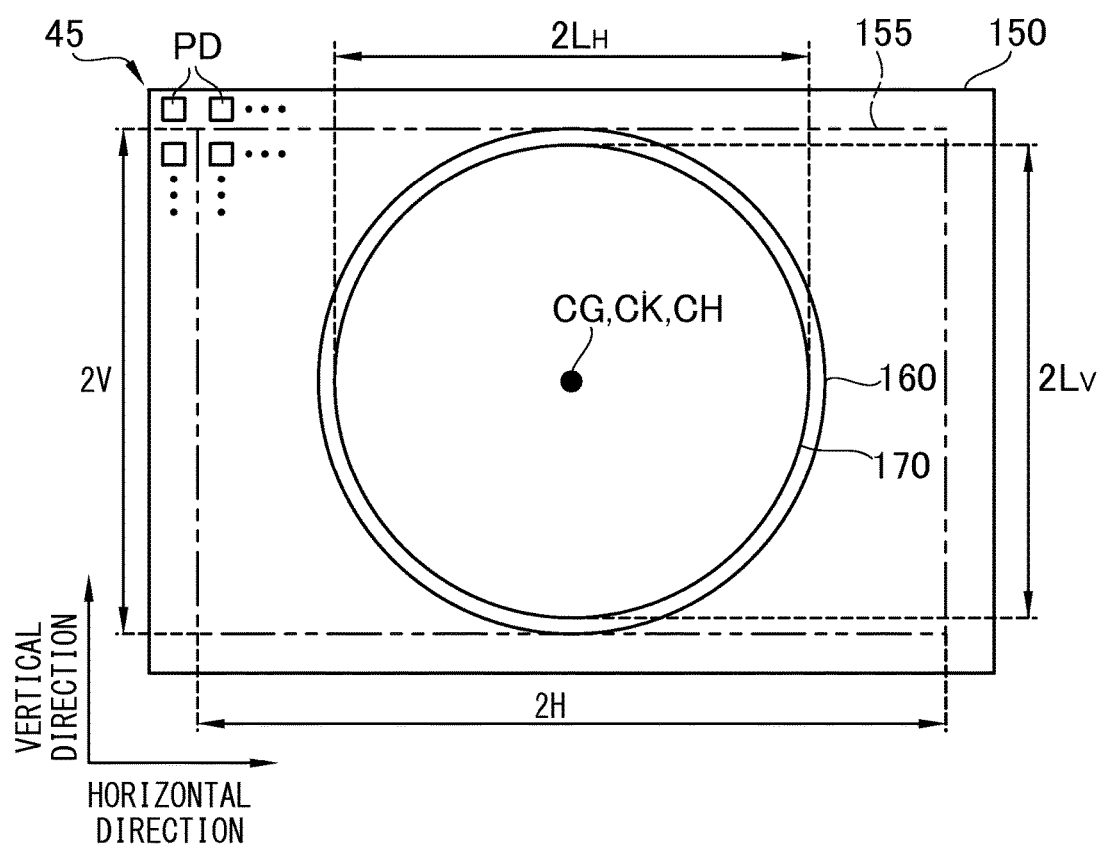
FIG. 3 is an explanatory view for describing a positional relationship among an effective pixel area, an imaging area and a display area, in an ideal state in which the center of the effective pixel area matches with the center of an observation optical system.
Figure 4:
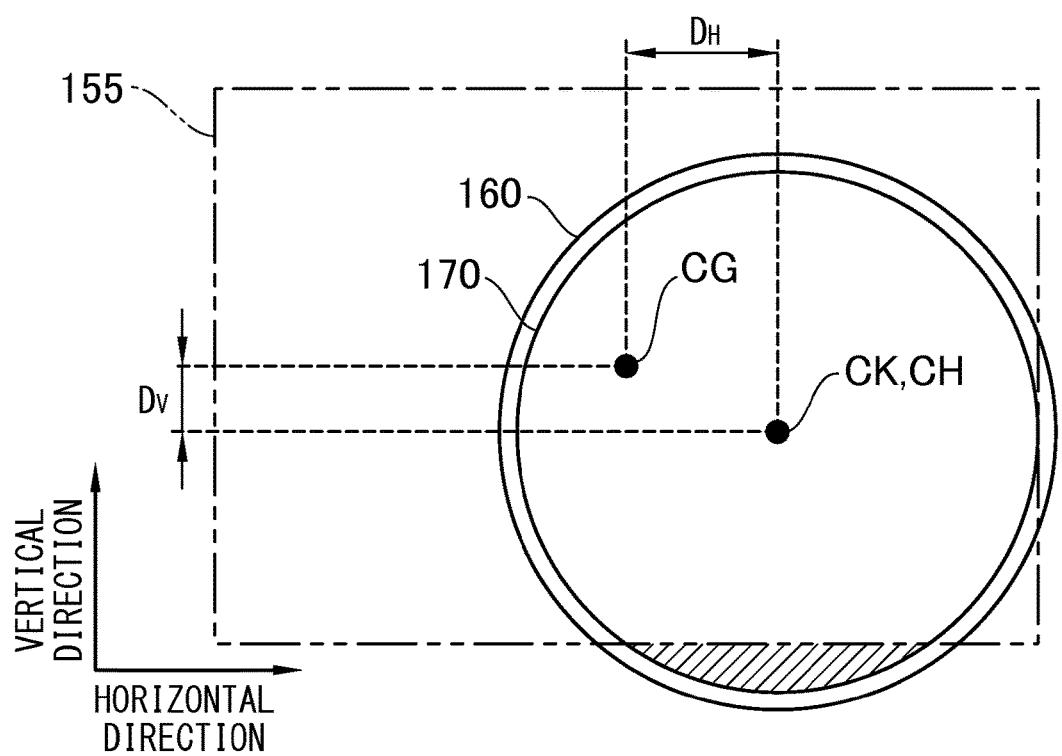
FIG. 4 is an explanatory view for describing a positional relationship among the effective pixel area, the imaging area and the display area, in an actual state in which deviation occurs between the center of the effective pixel area and the center of the observation optical system.

FIG. 3 is an explanatory view for describing a positional relationship among an effective pixel area 150 (displayable pixel area 155), an imaging area 160 and a display area 170, in an ideal state in which the center of the effective pixel area 150 (displayable pixel area 155) of a solid-state imaging element 45 matches with the center of an observation optical system 44. In addition, FIG. 4 is an explanatory view for describing a positional relationship among the effective pixel area 150, the imaging area 160 and the display area 170, in an actual state in which deviation occurs between the center of the effective pixel area 150 of the solid-state imaging element 45 and the center of the observation optical system 44.

As shown in FIG. 3, the effective pixel area 150 is a pixel area in which signals of pixels are used as signals that have been actually imaged, on the imaging plane of the solid-state imaging element 45, and is a pixel area having a rectangular shape in the present embodiment.

In addition, the effective pixel area 150 contains a displayable pixel area 155 which is an area that is used for display of an image in the monitor 14. Specifically, the displayable pixel area 155 is an area which excludes a portion that is used in image processing and the like and a margin of several pixels, from the effective pixel area 150. The displayable pixel area 155 in the present embodiment is a pixel area having a rectangular shape, and the number of pixels in a vertical direction and a horizontal direction thereof are "2V" and "2H", respectively. In the present embodiment, in order to prevent complication of the drawings, the position of a pixel area center CG which is the center of the effective pixel area 150 is matched with the position of the center of the displayable pixel area 155. Accordingly, the pixel area center CG corresponds to the center of the displayable pixel area 155. Incidentally, the position of the center of the displayable pixel area 155 may deviate from the position of the center of the effective pixel area 150.

The imaging area 160 is an area of an optical image which is formed on the imaging plane of the solid-state imaging element 45 by the observation optical system 44, and is a circular area in the present embodiment.

The display area 170 is a display area in which a site to be observed in an image which has been subjected to masking process that will be described later is displayed on the monitor 14. The display area 170 in the present embodiment is a circular area, and the maximum numbers of pixels in a vertical direction thereof and a horizontal direction thereof are "$2L_V$" and "$2L_H$" ($2L_V=2L_H$), respectively.

In the present embodiment, a display area center CH that is the center of the display area 170 is matched with an imaging area center CK which is the center of the imaging area 160, in a similar way to that of the above described Japanese Patent No. 4772826. The display area center CH can be matched with the imaging area center CK, for instance, by a process of cutting out image data for display from the image data which is input from the DSP 63 with reference to the imaging area center CK. Thereby, an observation image having no angle of deviation is obtained.

The image cutting-out information 51 is information that specifies an image cutting-out region TR (see FIG. 5) for a process of cutting out the image data for display, which corresponds to the display area 170 to be displayed on the monitor 14, from the image data which is output from the DSP 63. This image cutting-out information 51 is information that specifies the image cutting-out region TR for a process of cutting out the image data for display, which corresponds to an overlapping region in which the displayable pixel area 155 and the imaging area 160 overlap one another, and overlap one another when the imaging area center CK is matched with the display area center CH.

In an ideal state as shown in FIG. 3, the position of the pixel area center CG matches with the position of the imaging area center CK, and accordingly all of the display area 170 is positioned in the displayable pixel area 155.

On the other hand, in the actual state, attachment accuracy of the solid-state imaging element 45 and the observation optical system 44 is low, and accordingly deviation occurs between the pixel area center CG and the imaging area center CK, as shown in FIG. 4. The reference character "$D_V$" in the figure designates a deviation amount in a vertical direction which is an amount of deviation between the pixel area center CG and the imaging area center CK in the vertical direction, and the reference character "$D_H$" in the figure designates a deviation amount in a horizontal direction which is an amount of deviation between the pixel area center CG and the imaging area center CK in the horizontal direction.

A margin of the effective pixel area 150 with respect to the imaging area 160, and a margin of the imaging area 160 with respect to the display area 170 each cannot be allocated, along with a tendency of miniaturization of the solid-state imaging element 45 and the observation optical system 44 in the electronic endoscope 11. For this reason, in the actual state, even though the display area center CH is matched with the imaging area center CK, a part (portion displayed by hatching in the figure) of a region in which the imaging area 160 and the display area 170 overlap one another is positioned in the outside of the displayable pixel area 155. As a result, a part of an optical image corresponding to the display area 170 is formed in the outside of the displayable pixel area 155.

Figure 5:
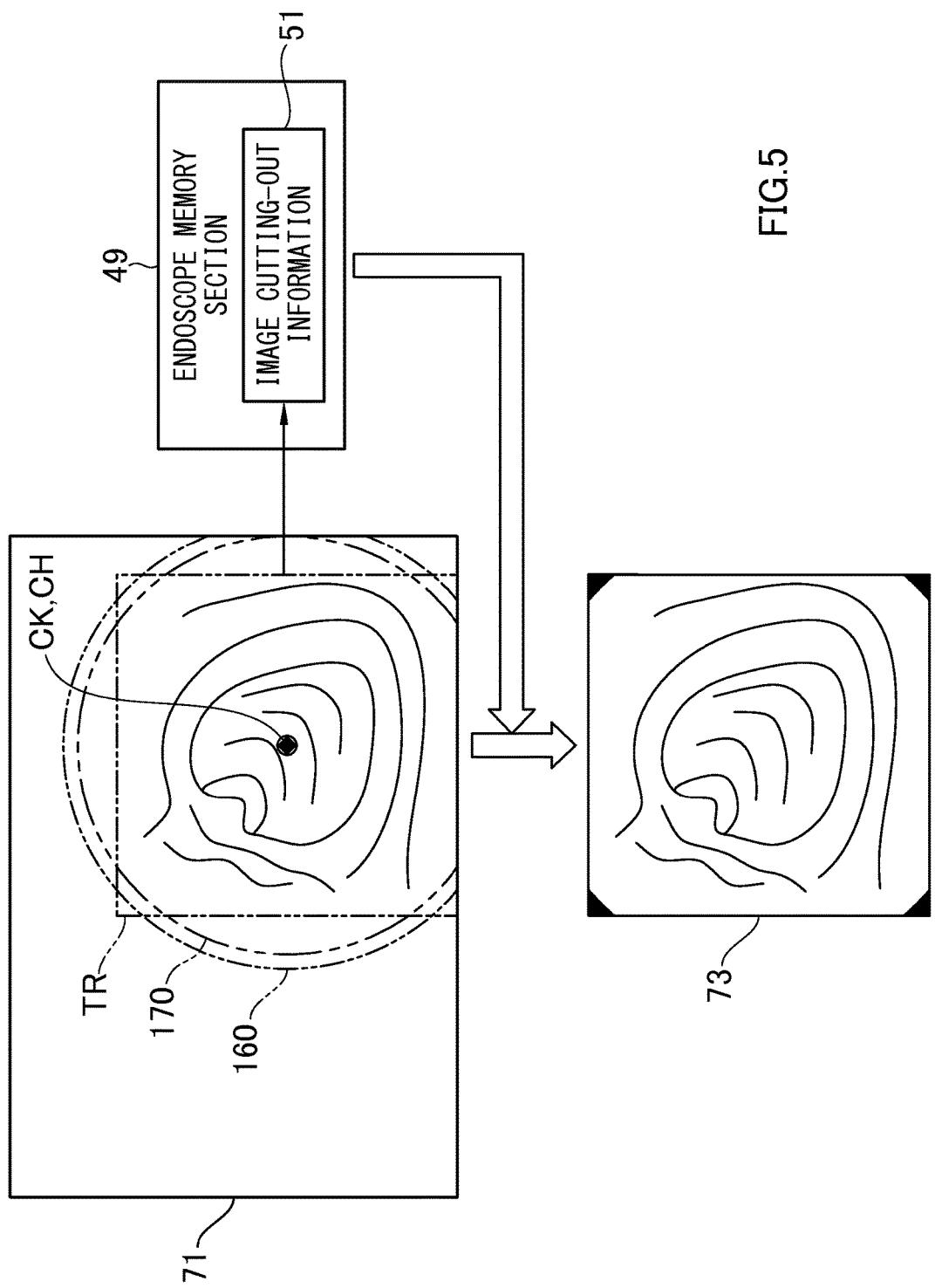
FIG. 5 is an explanatory view for describing an image cutting-out region and image cutting-out information.

FIG. 5 is an explanatory view for describing an image cutting-out region TR and image cutting-out information 51, in the actual state. As shown in FIG. 5, the image cutting-out region TR is the largest region which has the same aspect ratio as that of the display area 170 with reference to the imaging area center CK, in an image on the basis of image data 71 which is input from the DSP 63. Incidentally, the display area 170 in the present embodiment is circular, and accordingly "region having the same aspect ratio" described here is, for instance, a square region.

Here, a position corresponding to the center of the image cutting-out region TR, that is, a position corresponding to the imaging area center CK (optical axis of observation optical system 44) in the image on the basis of the image data 71 is determined, for instance, by a process of photographing various test charts such as a concentric circular pattern, with the electronic endoscope 11, and analyzing image data which has been obtained by this photographing. In addition, the shape and the size of the display area 170 are known. Accordingly, the image cutting-out region TR can be determined, on the basis of the position of the imaging area center CK, and the shape and the size of the display area 170. This information which shows the position, the size and the like of the image cutting-out region TR is previously determined as the image cutting-out information 51 when the electronic endoscope 11 is manufactured, and is stored in the endoscope memory section 49. Thereby, the image data 73 for display, which corresponds to the image cutting-out region TR, can be cut out from the image data 71, on the basis of the image cutting-out information 51.

In addition, the image cutting-out information 51 in the present embodiment is information which shows the image cutting-out region TR in the case where attachment accuracy of the solid-state imaging element 45 and the like is low, and when the display area center CH is matched with the imaging area center CK, a part of the display area 170 is positioned in the outside of the displayable pixel area 155, as shown in FIG. 4. That is, the image cutting-out information 51 is information which shows the image cutting-out region TR in the case where at least either of the following Expression (1) and Expression (2) is satisfied. Accordingly, the numbers of pixels (pixel sizes) of the image data 73 for display in the vertical direction and the horizontal direction become smaller than the numbers of pixels $2L_V$ and $2L_H$ of the display area 170 in the vertical direction and the horizontal direction, respectively.

[Expression 1]

$$V-L_V \leq D_V \qquad (1)$$

[Expression 2]

$$H-L_H \leq D_H \qquad (2)$$

[Magnification Information]

Figure 6:
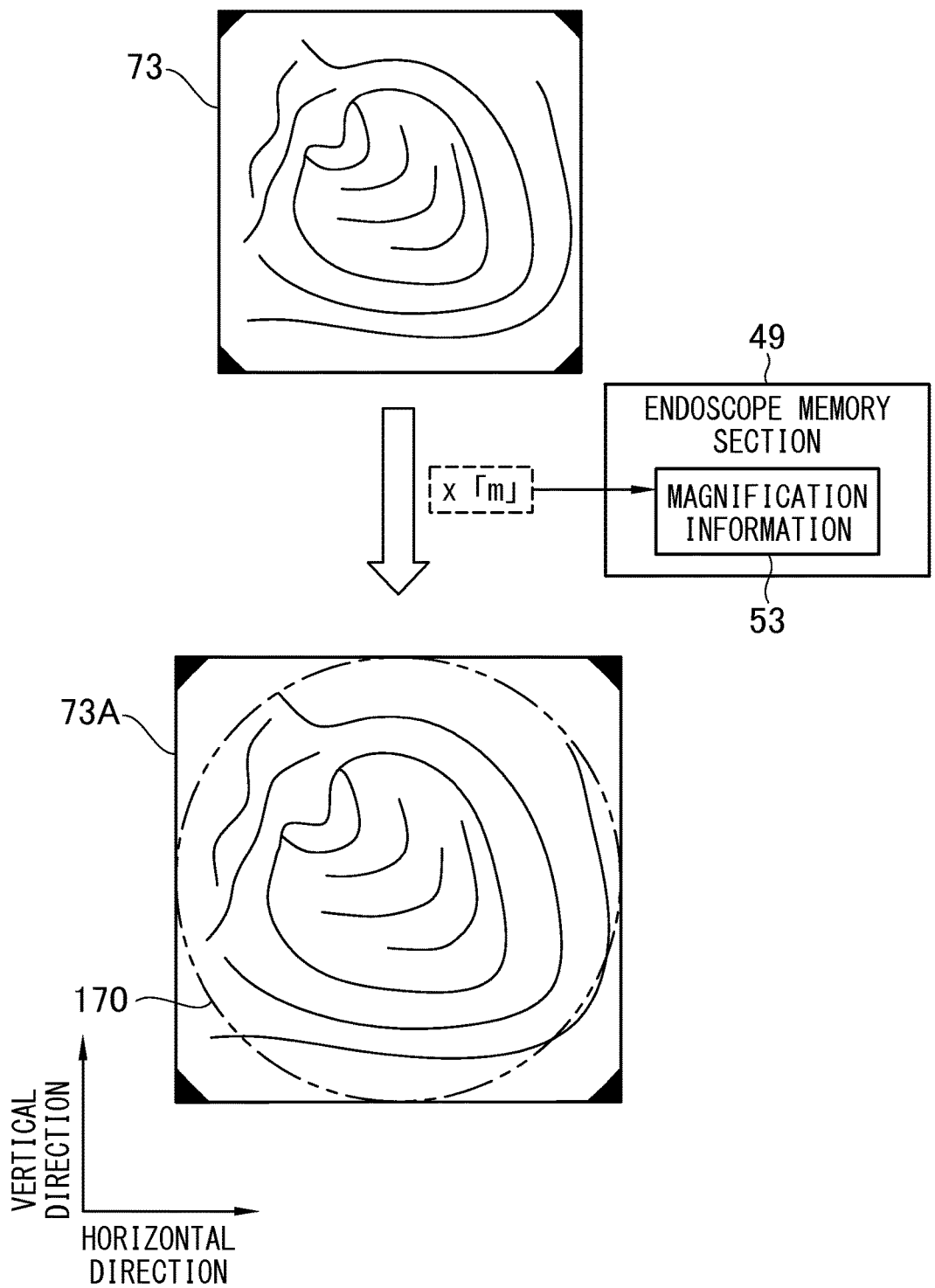
FIG. 6 is an explanatory view for describing magnification information.

FIG. 6 is an explanatory view for describing magnification information 53. As shown in FIG. 6, the magnification information 53 is information which shows the magnification m for a process of expanding the image data 73 for display to the image size of the display area 170. As for the magnification m, the higher magnification m is selected out of the magnifications m expressed by the following Expression (3) and Expression (4). In addition, the magnification m is previously determined when the electronic endoscope 11 is manufactured, and is stored in the endoscope memory section 49 as the magnification information 53, in a similar way to the above described image cutting-out information 51. Thereby, the image data 73A for display is obtained, which is formed by a process of expanding the image data 73 for display to the image size of the display area 170, on the basis of the magnification information 53.

[Expression 3]

$$m=L_V/(V-D_V) \qquad (3)$$

[Expression 4]

$$m=L_H/(H-D_H) \qquad (4)$$

Incidentally, when any of the above described Expression (1) and Expression (2) is not satisfied, or when the magnification m is higher than twice which is an admissible magnification (in the case of m>2), the magnification m is set at m=1, and the image is not expanded. This is because when any of the above described Expression (1) and Expression (2) is not satisfied, all of the display area 170 is positioned in the displayable pixel area 155 in a state in which the display area center CH is matched with the imaging area center CK (see FIG. 3), and accordingly the image data 73 for display does not need to be expanded.

In addition, the case in which the magnification m is higher than the admissible magnification "twice" (m>2) is the case in which the attachment accuracy of the solid-state imaging element 45 and the observation optical system 44 becomes remarkably low, and an amount of deviation between the pixel area center CG and the imaging area center CK becomes large. In this case, the image size of the image data 73 for display becomes small, and accordingly the magnification m needs to be increased for a process of expanding the image data 73 for display to the image size of the display area 170, but when the expansion magnification of the image data 73 for display exceeds twice, the image quality generally deteriorates. Because of this, when the magnification m becomes m≤2, that is, when the magnification m becomes the admissible magnification or less, the image is expanded. Incidentally, the admissible magnification is not limited to "twice", but is appropriately determined according to the image size of the display area 170 and the like.

[Configuration of Image Processing Section]

Figure 7:
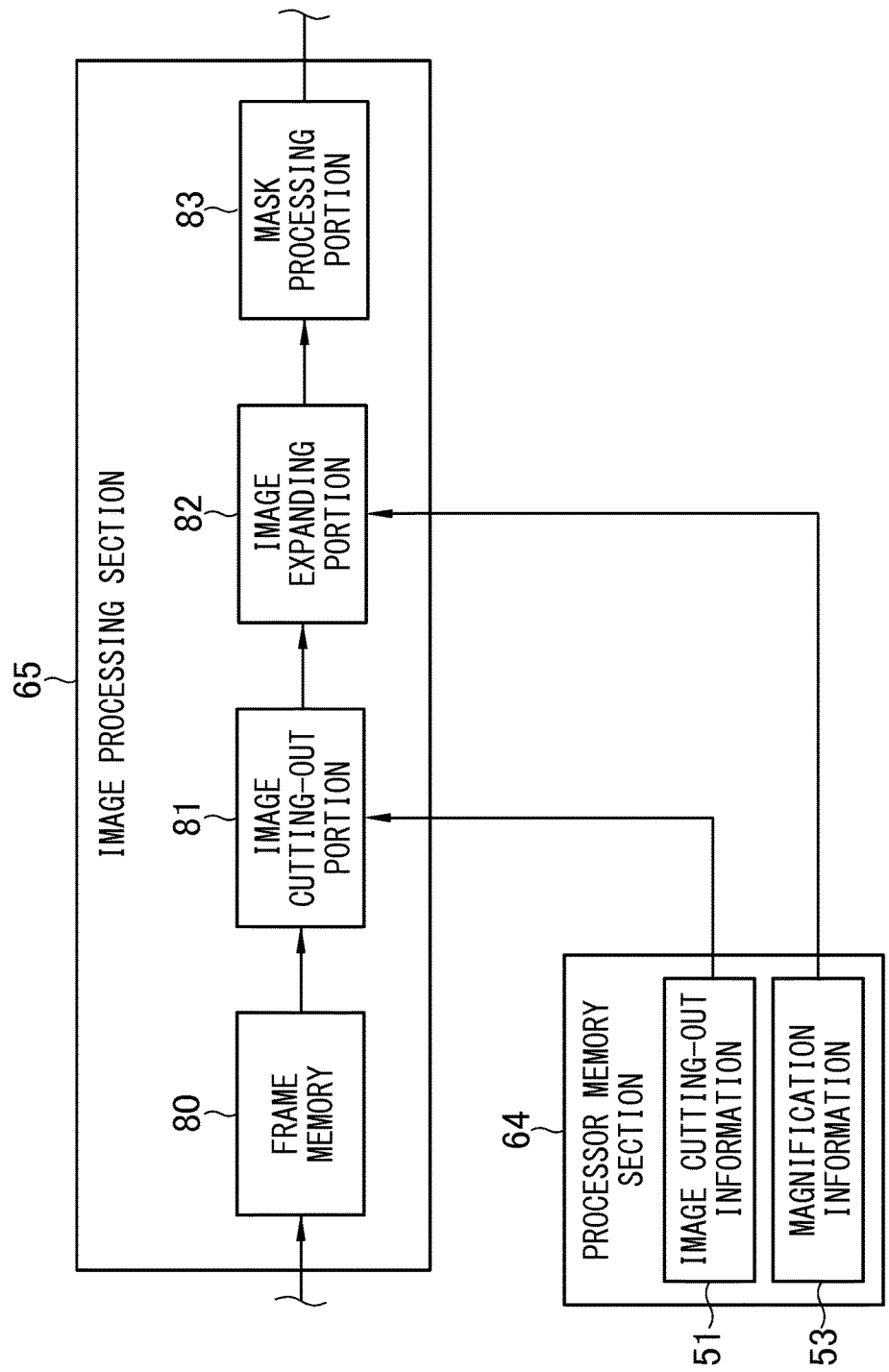
FIG. 7 is a functional block diagram of the image processing section shown in FIG. 2.

FIG. 7 is a functional block diagram of an image processing section 65. As shown in FIG. 7, the image processing section 65 has a frame memory 80, an image cutting-out portion 81, an image expanding portion 82 and a mask processing portion 83.

The frame memory 80 is a memory which temporarily stores image data 71 for every one frame which is input from the DSP 63, and simultaneously stores the image data 71 for a plurality of frames. Incidentally, new image data 71 which is input from the DSP 63 is overwritten on the oldest image data 71 in the data which is stored in the frame memory 80.

The image cutting-out portion 81 reads out image data 71 which has been newly recorded from the frame memory 80, and cuts out the image data 73 for display from the image data 71, on the basis of the image cutting-out information 51 which has been acquired from a processor memory section 64, as shown in FIG. 5. The image cutting-out portion 81 outputs the cut-out image data 73 for display to the image expanding portion 82.

The image expanding portion 82 electronically expands the image data 73 for display, which has been input from the image cutting-out portion 81, at the magnification m, on the basis of the magnification information 53 that has been acquired from the processor memory section 64, and generates the image data 73A for display, as shown in FIG. 6. The image expanding portion 82 outputs the generated image data 73A for display to the mask processing portion 83.

Figure 8:
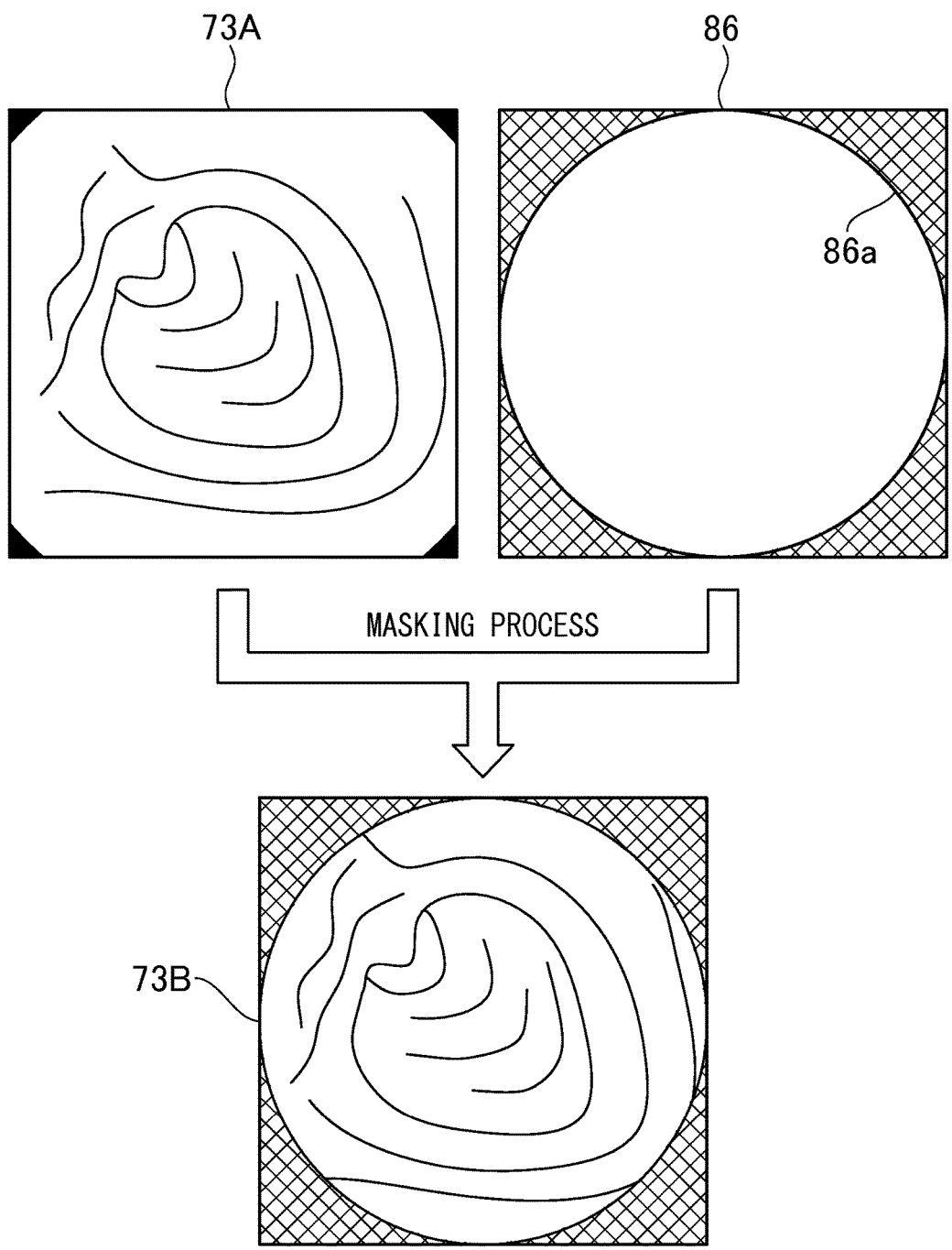
FIG. 8 is an explanatory view for describing a masking process by a mask processing portion.

FIG. 8 is an explanatory view for describing a masking process in a mask processing portion 83. As shown in FIG. 8, the mask processing portion 83 conducts the masking process of masking the image data 73A for display while keeping the same shape as that of the display area 170, on the basis of the mask image data 86, and generates the image data 73B for display. The mask image data 86 is a rectangular image having the same size as that of the image data 73A for display. The mask image data 86 has an exposing portion 86*a* which exposes only the display area 170.

The masking process is conducted by a method of: outputting pixels corresponding to the inside of the display area 170 as they are, on the basis of the mask image data 86, while passing each pixel in the image data 73A for display, in the mask processing portion 83; discarding pixels corresponding to the outside of the display area 170; and outputting mask pixels in place of the discarded pixels. The mask pixels are video signals corresponding to the color of the mask image. The mask processing portion 83 outputs the image data 73B for display, which has been subjected to the masking process, to the display driver 66. Thereby, the observation image of the site to be observed on the basis of the image data 73B for display is displayed on the monitor 14 by the display driver 66.

[Image Adjusting Method for Endoscope Apparatus]

Figure 9:
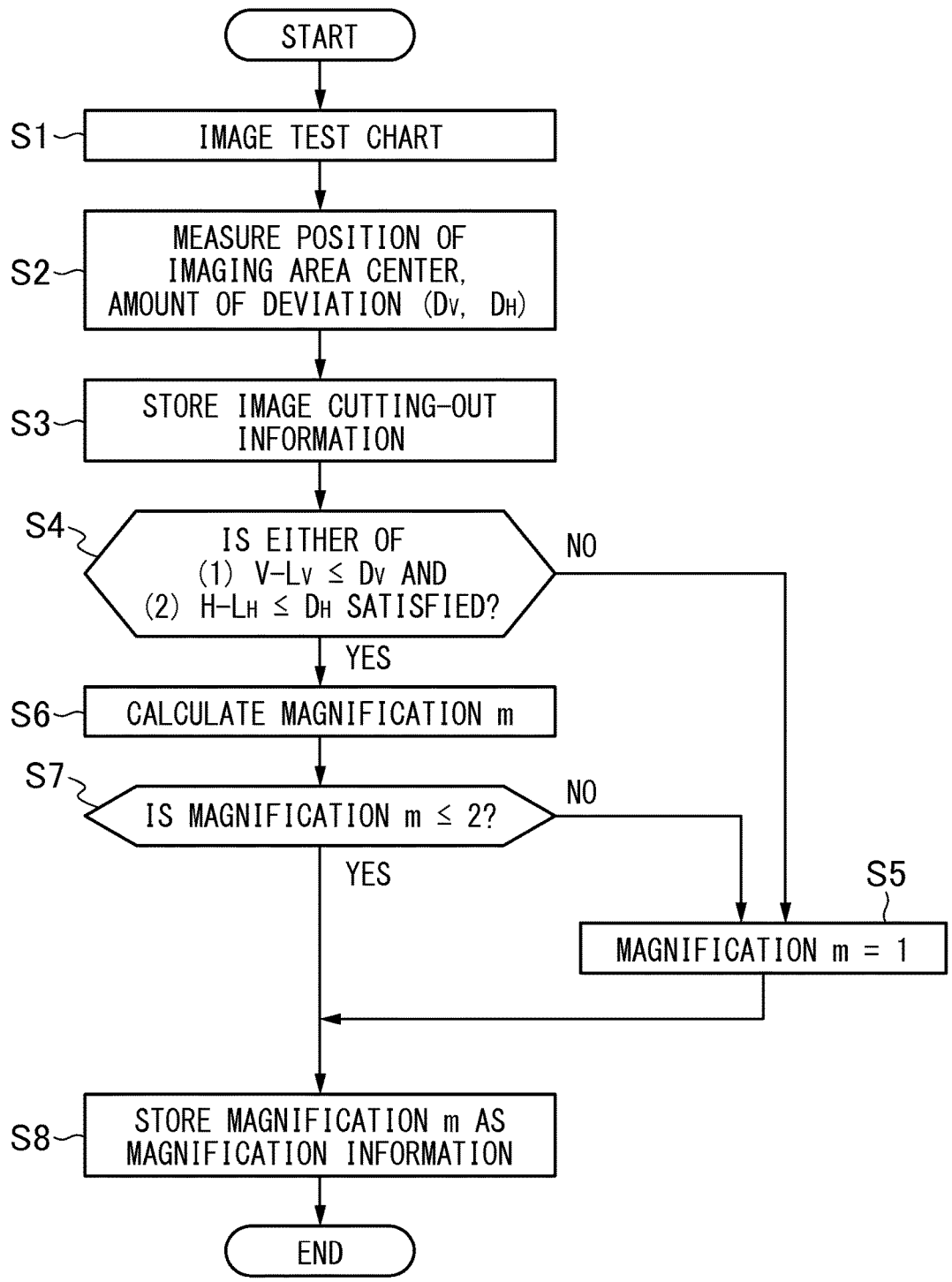
FIG. 9 is a flow chart showing a flow of steps for storing the image cutting-out information and the magnification information, which is a part of steps in a process of manufacturing an electronic endoscope.
Figure 10:
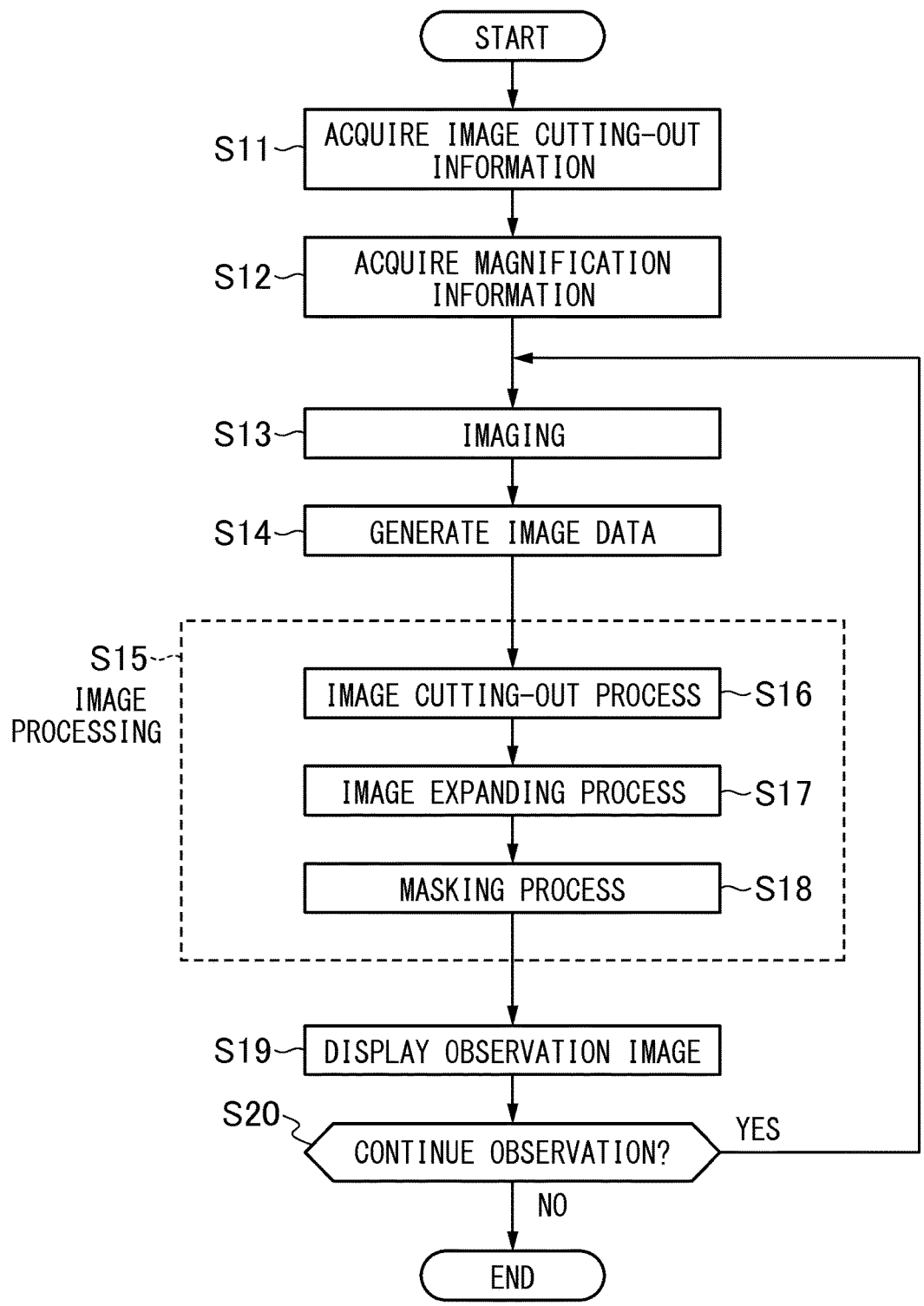
FIG. 10 is a flow chart showing a flow of a process for displaying an observation image, which includes image processing according to an image adjusting method of the present invention.
Figure 11:
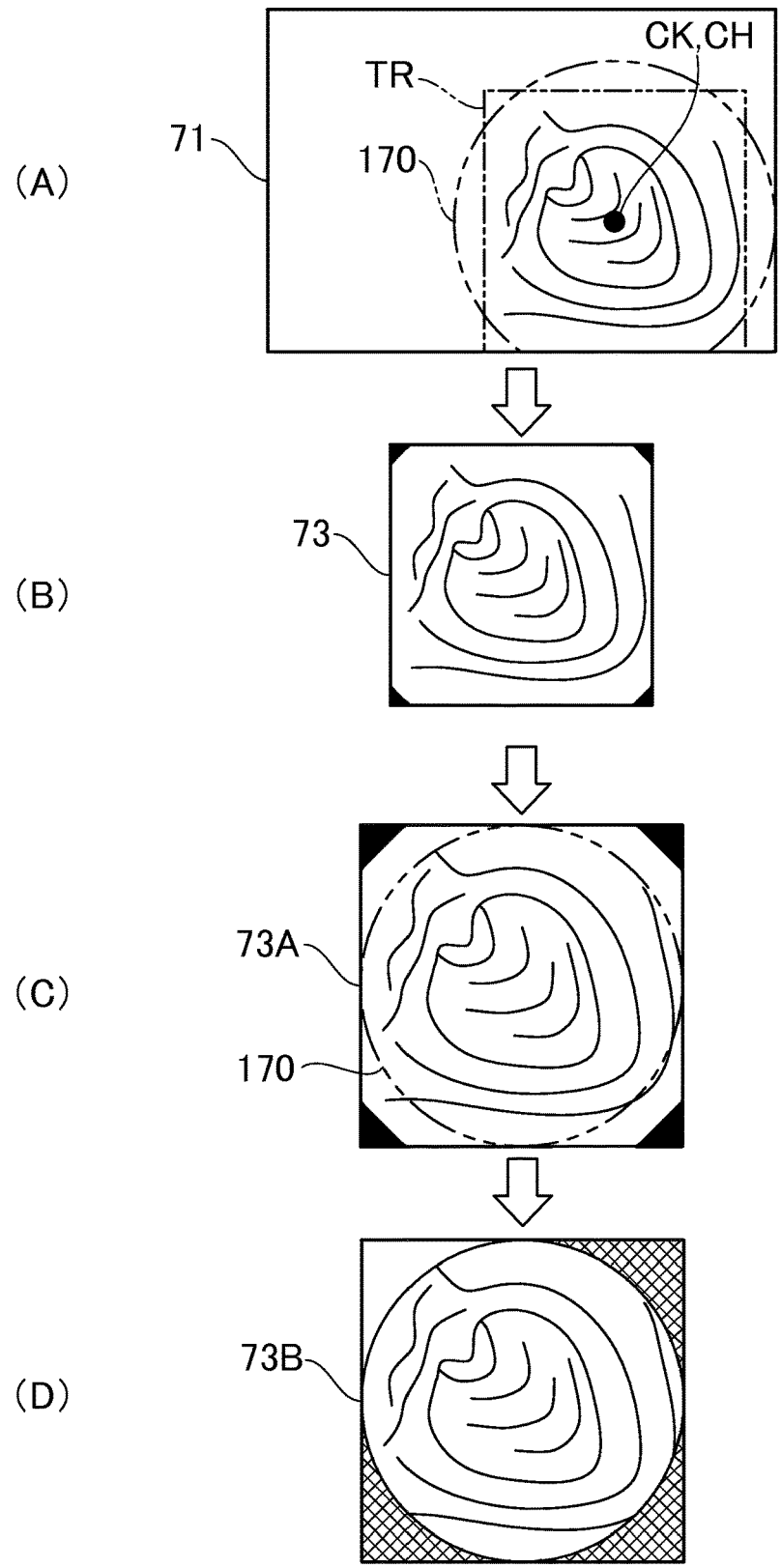
FIG. 11 is an explanatory view for describing the image processing according to the image adjusting method of the present invention.

Next, the image adjusting method for the endoscope apparatus 10 having the above described structure will be described with reference to FIG. 9 to FIG. 11. FIG. 9 is a flow chart which is a part of a process of manufacturing an electronic endoscope 11, and shows a flow of steps for storing the image cutting-out information 51 and the magnification information 53 that are used in image processing according to the image adjusting method of the present invention. FIG. 10 is a flow chart showing a flow of a process for displaying an observation image, which includes the image processing according to the image adjusting method of the present invention. FIG. 11 is an explanatory view for describing the image processing according to the image adjusting method of the present invention.

<Steps for Storing Image Cutting-Out Information and Magnification Information>

As shown in FIG. 9, after an assembly of an imaging module containing an observation optical system 44 and a solid-state imaging element 45 of an electronic endoscope 11 has been completed (the timing after assembly of electronic endoscope 11 has been completed is also acceptable), a test chart is imaged by the imaging module (step S1). The image data which has been obtained by the imaging of the test chart is analyzed, and thereby a position corresponding to the imaging area center CK, the amount of deviation $D_V$ in a vertical direction and the amount of deviation $D_H$ in a horizontal direction, in the image, are determined on the basis of the image data 71 (step S2).

Subsequently, the image cutting-out region TR is determined, on the basis of the position corresponding to the imaging area center CK and the shape and size of the known display area 170, and the image cutting-out information 51 which shows this image cutting-out region TR is stored in the endoscope memory section 49 (step S3).

In addition, it is confirmed whether the amount of the deviation $D_V$ in the vertical direction and the amount of the deviation $D_H$ in the horizontal direction satisfy at least either of the above described Expression (1) and Expression (2) or not (step S4), and when the amounts do not satisfy any of the expressions, the magnification m is determined to be m=1 (No in step S4, and step S5).

On the other hand, when the amount of the deviation $D_V$ in the vertical direction and the amount of the deviation $D_H$ in the horizontal direction satisfy at least either of the above described Expression (1) and Expression (2), the magnifications m are determined on the basis of the above described Expression (3) and Expression (4), respectively (Yes in step S4, and step S6). Then, it is confirmed whether the higher magnification out of the determined magnifications m satisfies m≤2 or not (step S7), and when the higher magnification satisfies m≤2, the higher magnification is determined to be the magnification m (Yes in step S7, and step S8). On the contrary, when the higher magnification becomes m>2, the magnification m is determined to be m=1 (No in step S7, and step S5).

Subsequently, the determined magnification m is stored in the endoscope memory section 49 as the magnification information 53 (step S8). With the above, the steps for storing the image cutting-out information 51 and the magnification information 53 are completed, which correspond to one aspect of the storing steps of the present invention.

<Process for Displaying Observation Image>

As shown in FIG. 10, firstly, the start-up of the endoscope apparatus 10 is started. Specifically, the connector portions 25*a* and 25*b* of the electronic endoscope 11 are connected to the light source device 12 and the processor device 13, respectively, and the power supplies of the light source device 12 and the processor device 13 are turned on. Thereby, the light source device 12 and the processor device 13 are started respectively, and the electronic endoscope 11 is started by an electric power supplied from the light source device 12 and the like.

When the electronic endoscope 11, the light source device 12 and the processor device 13 are started, the endoscope CPU 47 transmits the image cutting-out information 51 and the magnification information 53 which are stored in the endoscope memory section 49, to the processor CPU 61. Thereby, the processor CPU 61 can acquire the image cutting-out information 51 and the magnification information 53. The processor CPU 61 makes the processor memory section 64 store the acquired image cutting-out information 51 and the magnification information 53.

Subsequently, the image cutting-out portion 81 acquires the image cutting-out information 51 from the processor memory section 64 (step S11), and the image expanding portion 82 acquires the magnification information 53 from the processor memory section 64 (step S12).

In addition, other necessary information is exchanged among the light source CPU 31, the endoscope CPU 47 and the processor CPU 61, and the start-up of the endoscope apparatus 10 is completed.

After the start-up of the endoscope apparatus 10 has been completed, the insertion section 16 of the electronic endoscope 11 is inserted into the patient body, and the site to be observed is imaged (step S13). The illuminating light which is supplied from the light source device 12 is emitted from the illumination window 42 toward the site to be observed through the light guide 40. The illuminating light which has been reflected or scattered on the site to be observed passes through the observation window 43, and is formed into an image on the imaging plane of the solid-state imaging element 45 as the optical image, by the observation optical system 44. The solid-state imaging element 45 converts the optical image which has been formed on the imaging plane, into an imaging signal, and outputs the converted signal to the DSP 63 of the processor device 13.

The DSP 63 subjects the image signal for one frame which has been input from the electronic endoscope 11 to various signal processes such as color interpolation, color separation, color balance adjustment, gamma correction and image enhancement processing, and generates the image data 71 for one frame (step S14). This image data 71 is output from the DSP 63 to the image processing section 65, and is temporarily stored in the frame memory 80 in the image processing section 65.

Subsequently, the image processing corresponding to one form of the image processing step of the present invention is started for the image data 71 which has been stored in the frame memory 80, by each portion in the image processing section 65 (step S15). Specifically, the image data 71 is subjected to the image cutting-out process (step S16), the image expanding process (step S17) and the masking process (step S18), in this order.

As shown in portions (A) and (B) of FIG. 11, the image cutting-out portion 81 conducts the image cutting-out process of reading out the image data 71 from the frame memory 80, and cutting out the image data 73 for display, which corresponds to the image cutting-out region TR, from the image data 71, on the basis of the previously acquired image cutting-out information 51. At this time, the image data 73 for display is cut out from the image data 71, with reference to the imaging area center CK, and thereby the display area center CH can be matched with the imaging area center CK. Thereby, an observation image having no angle of deviation is obtained. The image data 73 for display is output from the image cutting-out portion 81 to the image expanding portion 82.

As shown in a portion (C) of FIG. 11, the image expanding portion 82 conducts the image expanding process of electronically expanding the image data 73 for display, which has been input from the image cutting-out portion 81, at the magnification m, on the basis of the previously acquired magnification information 53. Thereby, the image data 73A for display is obtained, which is formed by a process of expanding the image data 73 for display to the image size of the display area 170. This image data 73A for display is output from the image expanding portion 82 to the mask processing portion 83.

As shown in a portion (D) of FIG. 11, the mask processing portion 83 subjects the image data 73A for display to the masking process, and generates the image data 73B for display. The image data 73B for display, which has been subjected to the masking process, is output from the mask processing portion 83 to the display driver 66.

The description returns to FIG. 10. The display driver 66 makes the monitor 14 display the observation image of the site to be observed, on the basis of the image data 73B for display, which is input from the mask processing portion 83 (step S19). Hereinafter, the processes from the above described step S13 to step S19 are repeatedly carried out until the imaging for the site to be observed ends (step S20).

Effect of the Invention

An endoscope apparatus 10 of the present invention cuts out the image data 73 for display from the image data 71 on the basis of the image cutting-out region TR that corresponds to an overlapping region in which a displayable pixel area 155 and an imaging area 160 overlap one another, and overlap one another when the display area center CH is matched with the imaging area center CK; expands the image data 73 for display to the image size of the display area 170; and makes the monitor 14 display the expanded image data. Thereby, an adequate observation image which shows no vignetting can be obtained, even though attachment accuracy of a solid-state imaging element 45 and an observation optical system 44 is low, and consequently a part of a portion corresponding to the display area 170 in the imaging area 160 is positioned in the outside of the displayable pixel area 155.

In addition, the endoscope apparatus 10 of the present invention makes the endoscope memory section 49 of the electronic endoscopes 11 previously store the image cutting-out information 51 and the magnification information 53, and thereby can easily adjust the image data for display to the image size of the display area 170, by only conducting the image cutting-out process and the image expanding process according to the image cutting-out information 51 and the magnification information 53. In addition, the image processing section 65 in the processor device 13 can carry out the image cutting-out process and the image expanding process, which adapt to the attachment accuracy of the solid-state imaging element 45 and the like in each of the electronic endoscopes 11.

In addition, in the endoscope apparatus 10 of the present invention, the image cutting-out region TR has the same aspect ratio as that of the display area 170, accordingly even when the image data for display are expanded, an angle of view of an observation image to be displayed on the monitor 14 becomes only slightly narrow to the eye, and an observation image free from a feeling of strangeness is obtained.

In addition, the endoscope apparatus 10 of the present invention conducts the image cutting-out process and the image expanding process, when at least either of the above described Expression (1) and Expression (2) is satisfied. Thereby, it is prevented that the image cutting-out process and the image expanding process are conducted when either of the above described Expression (1) and Expression (2) is not satisfied, that is, even when such above described processes do not need to be carried out so as to position all of the display area 170 in the displayable pixel area 155 in the state in which the display area center CH is matched with the imaging area center CK.

In addition, the endoscope apparatus 10 of the present invention conducts the image expanding process, when the higher magnification m out of the magnifications m becomes m≤2, which have been determined on the basis of the above described Expression (3) and Expression (4). Thereby, it is prevented that the image data 73 for display is expanded to the image size of the display area 170 in the case of m>2, that is, in the case where the amount of deviation between the pixel area center CG and the imaging area center CK becomes large, and the image size of the image data 73 for display becomes small. Thereby, it is prevented that an observation image of poor image quality is displayed.

Other Example 1 of Endoscope Apparatus

Figure 12:
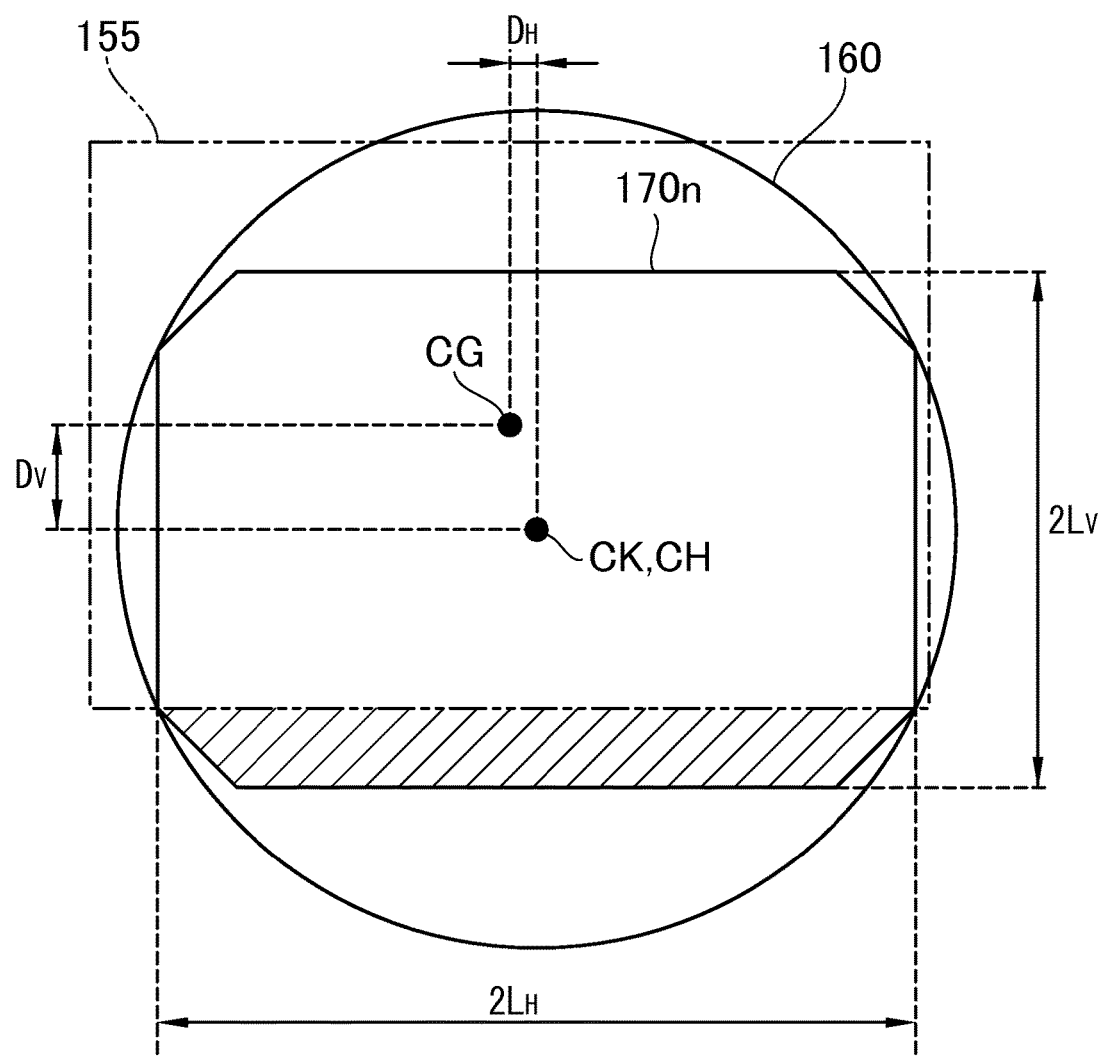
FIG. 12 is an explanatory view for describing a positional relationship among an effective pixel area (displayable pixel area), an imaging area and a display area in an endoscope apparatus in Other Example 1.
Figure 13:
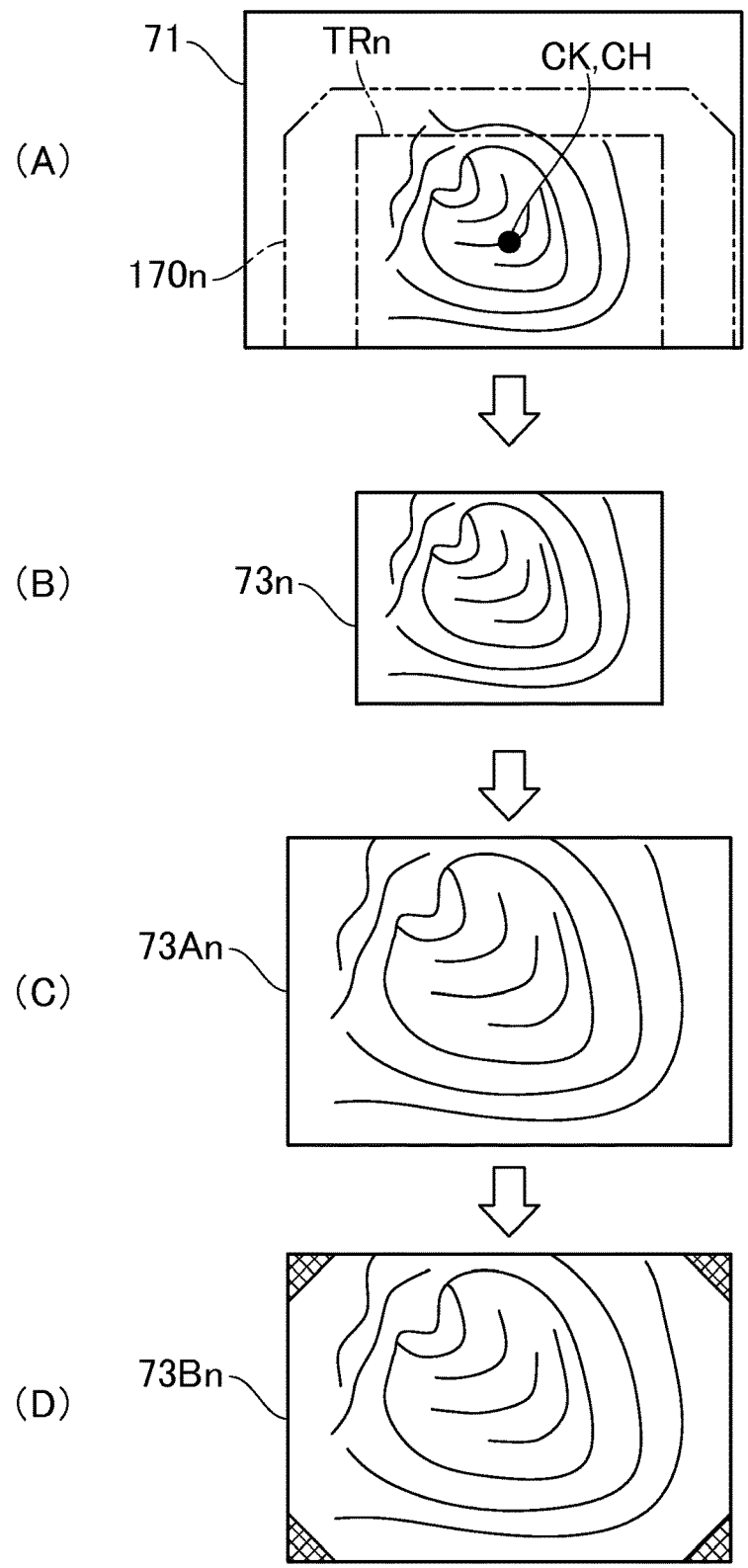
FIG. 13 is an explanatory view for describing image processing which is carried out in an endoscope apparatus in other Example 1.

Next, Other Example 1 of the endoscope apparatus of the present invention will be described with reference to FIG. 12 and FIG. 13. FIG. 12 is an explanatory view for describing a positional relationship among an effective pixel area 150 (displayable pixel area 155), an imaging area 160 and a display area 170$n$, in an endoscope apparatus of Other Example 1. FIG. 13 is an explanatory view for describing image processing which is carried out in the endoscope apparatus of Other Example 1.

In the endoscope apparatus 10 of the above described embodiment, the display area 170 is formed into a circular shape, but the display area 170$n$ may be formed into an approximately rectangular shape as that in the endoscope apparatus of Other Example 1, which is shown in FIG. 12. Incidentally, the endoscope apparatus of Other Example 1 has basically the same configuration as that of the endoscope apparatus 10 in the above described embodiment, except the point that the shape of the display area 170n is different, accordingly sections and portions having the same function and configuration as those in the above described embodiment are designated by the same reference characters and reference numerals, and the description will be omitted.

As shown in a portion (A) of FIG. 13, when the display area 170n has the approximately rectangular shape, an image cutting-out region TRn becomes the largest rectangular region having the same aspect ratio as that of the display area 170n with reference to the imaging area center CK, in the image on the basis of the above described image data 71. In addition, the image cutting-out information 51 which shows this image cutting-out region TRn is stored in the endoscope memory section 49. In addition, the magnification m is determined in a similar way to that in the above described embodiment, and is stored in the endoscope memory section 49 as the magnification information 53.

Hereinafter, the image cutting-out portion 81 conducts an image cutting-out process of cutting out image data 73n for display, which corresponds to the image cutting-out region TRn, from the image data 71, as shown in a portion (B) of FIG. 13, on the basis of the image cutting-out information 51, in a similar way to that in the above described embodiment. Then, the image expanding portion 82 conducts an image expanding process of expanding the image data 73n for display at the magnification m on the basis of the magnification information 53, and generates image data 73An for display, as shown in a portion (C) of FIG. 13.

Subsequently, the mask processing portion 83 subjects the image data 73An for display to a masking process, generates image data 73Bn for display, and outputs the generated image data to the display driver 66, as shown in a portion (D) of FIG. 13. Thereby, an observation image of a site to be observed on the basis of the image data 73Bn for display is displayed on the monitor 14 by the display driver 66. The endoscope apparatus of Other Example 1 has basically the same configuration as that of the endoscope apparatus 10 in the above described embodiment, except the point that the shape of the display area 170n is different, and accordingly can obtain a similar effect to the effect described in the above described embodiment.

Other Example 2 of Endoscope Apparatus

Figure 14:
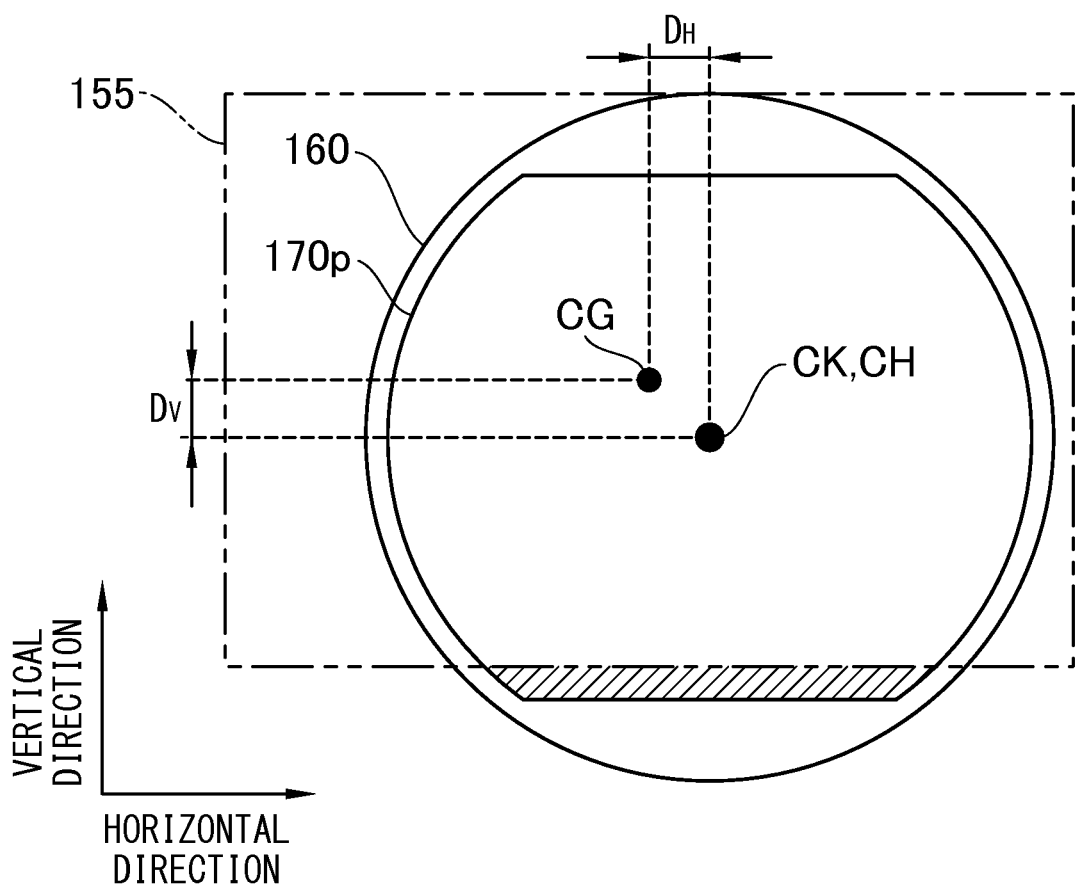
FIG. 14 is an explanatory view for describing a positional relationship among an effective pixel area (displayable pixel area), an imaging area and a display area in an endoscope apparatus in other Example 2.
Figure 15:
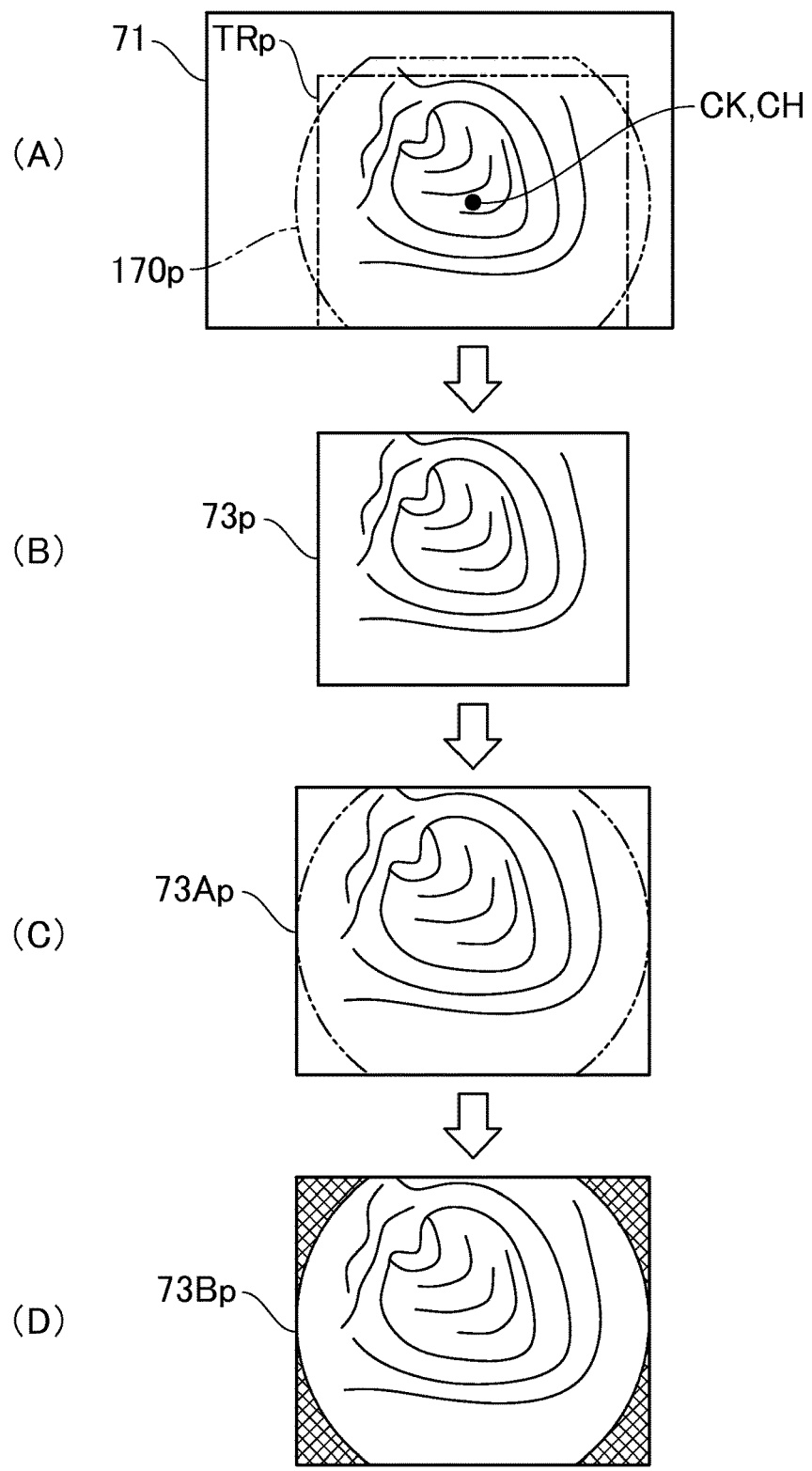
FIG. 15 is an explanatory view for describing image processing which is carried out in the endoscope apparatus in Other Example 2.

Next, Other Example 2 of the endoscope apparatus of the present invention will be described with reference to FIG. 14 and FIG. 15. FIG. 14 is an explanatory view for describing a positional relationship among an effective pixel area 150 (displayable pixel area 155), an imaging area 160 and a display area 170p, in an endoscope apparatus of Other Example 2. FIG. 15 is an explanatory view for describing image processing which is carried out in the endoscope apparatus of Other Example 2.

In the endoscope apparatus 10 of the above described embodiment, the display area 170 is formed into a circular shape, but the display area 170p may be formed into an approximately circular shape as that in the endoscope apparatus of Other Example 2, which is shown in FIG. 14. Incidentally, the endoscope apparatus in Other Example 2 also has basically the same configuration as that of the endoscope apparatus 10 in the above described embodiment, except the point that the shape of the display area 170p is different, accordingly sections and portions having the same function and configuration as those in the above described embodiment are designated by the same reference characters and reference numerals, and the description will be omitted.

As shown in a portion (A) of FIG. 15, when the display area 170p has the approximately circular shape, an image cutting-out region TRp becomes the largest rectangular region having the same aspect ratio as that of the display area 170p with reference to the imaging area center CK, in the image on the basis of the above described image data 71. In addition, the image cutting-out information 51 which shows this image cutting-out region TRp is stored in the endoscope memory section 49. In addition, the magnification m is determined in a similar way to that in the above described embodiment, and is stored in the endoscope memory section 49 as the magnification information 53.

Hereinafter, the image cutting-out portion 81 conducts an image cutting-out process of cutting out image data 73p for display, which corresponds to the image cutting-out region TRp, from the image data 71, as shown in a portion (B) of FIG. 15, on the basis of the image cutting-out information 51, in a similar way to that in the above described embodiment. Then, the image expanding portion 82 conducts an image expanding process of expanding the image data 73p for display at the magnification m on the basis of the magnification information 53, and generates image data 73Ap for display, as shown in a portion (C) of FIG. 15.

Subsequently, the mask processing portion 83 subjects the image data 73Ap for display to a masking process, generates image data 73Bp for display, and outputs the generated image data to the display driver 66, as shown in a portion (D) of FIG. 15. Thereby, an observation image of a site to be observed on the basis of the image data 73Bp for display is displayed on the monitor 14 by the display driver 66. The endoscope apparatus of Other Example 2 has basically the same configuration as that of the endoscope apparatus 10 in the above described embodiment, except the point that the shape of the display area 170p is different, and accordingly can obtain a similar effect to the effect described in the above described embodiment.

Incidentally, the shape and the size of the effective pixel area, the displayable pixel area, the imaging area and the display area are not limited to the shape and the size shown by each of the above described embodiments, and may be appropriately changed.

Other Example 3 of Endoscope Apparatus

Figure 16:
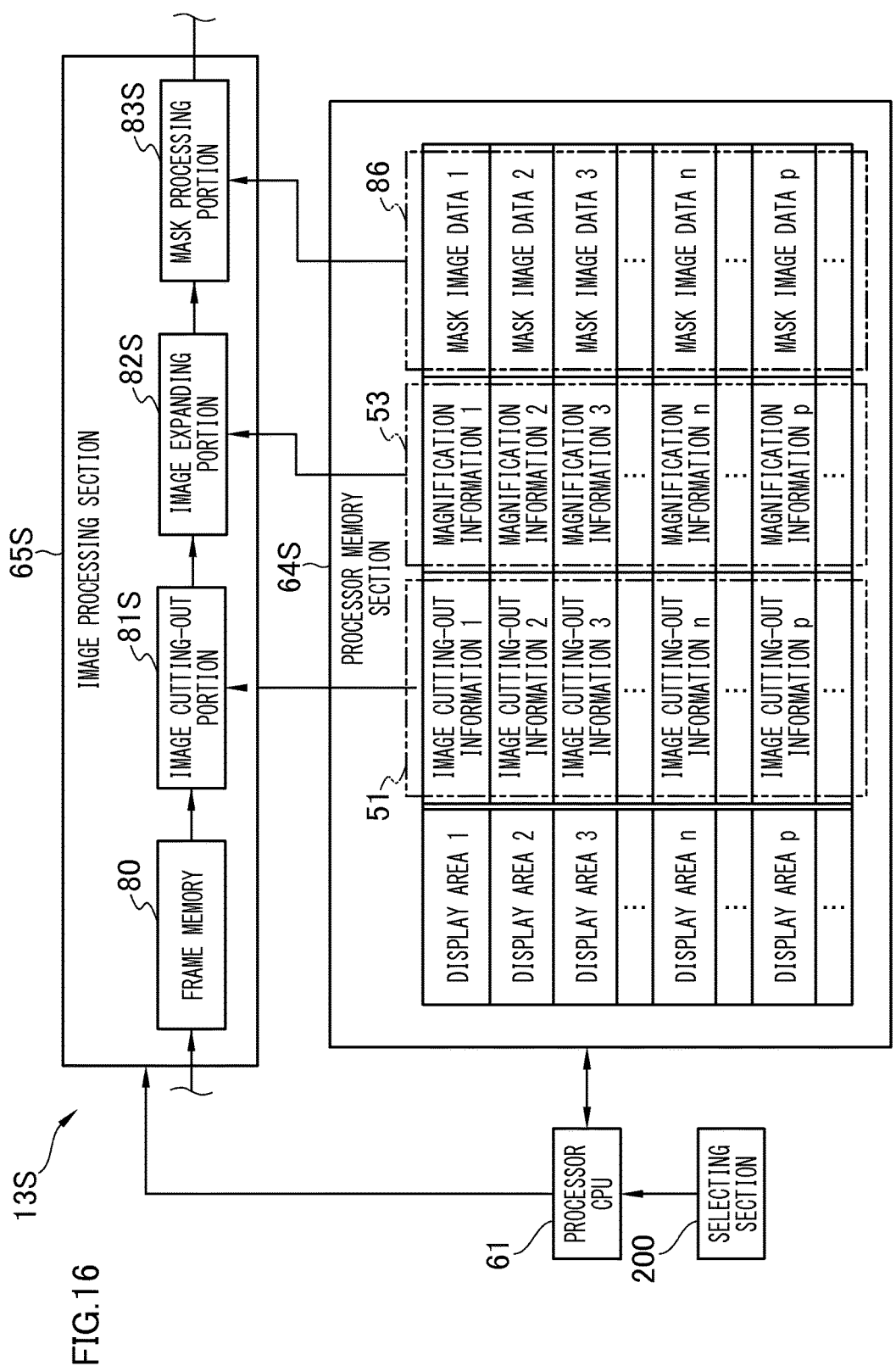
FIG. 16 is a block diagram showing an electrical configuration of an essential part of a processor device of an endoscope apparatus in Other Example 3.

Next, Other Example 3 of the endoscope apparatus of the present invention will be described with reference to FIG. 16. FIG. 16 is a block diagram showing an electrical configuration of an essential part of a processor device 13S in an endoscope apparatus of Other Example 3. In the endoscope apparatus 10 of the above described embodiment, the number of patterns of the display area 170 is one, but in the endoscope apparatus of Other Example 3, one display area can be selected from a plurality of patterns of the display area, that is, the display area is made to be switchable.

As shown in FIG. 16, the processor device 13S has basically the same configuration as that of the processor device 13 in the above described embodiment except the point that the processor device 13S is provided with a processor memory section 64S, an image processing section 65S and a selecting section 200, accordingly sections and portions having the same function and configuration as those in the above described embodiment are designated by the same reference characters and reference numerals, and the description will be omitted.

The processor memory section 64S stores a plurality of patterns of the display area, the image cutting-out information 51, the magnification information 53 and the mask image data 86 therein, in a form of being associated with each other. In other words, the processor memory section 64S has the image cutting-out information 51, the magnification information 53 and the mask image data 86 stored therein, which respectively correspond to the plurality of patterns of the display area. Incidentally, these information may be stored in the endoscope memory section 49 instead of being stored in the processor memory section 64S, and these information may be acquired from the endoscope memory section 49.

The selecting section 200 is provided, for instance, in an operation panel of the processor device 13S, and is operated when a user performs selection or switching of the display area. If a user performs the selection or switching operation of the display area through the selecting section 200, the display area information which shows the selected or switched display area is input into the image processing section 65S from the processor CPU61.

The image processing section 65S has the frame memory 80, an image cutting-out portion 81S, an image expanding portion 82S and a mask processing portion 83S.

The image cutting-out portion 81S reads out the image cutting-out information 51 corresponding to the display area which has been selected or switched in the selecting section 200, from the processor memory section 64S, on the basis of the display area information that has been input from the processor CPU61. Then, the image cutting-out portion 81S cuts out the image data for display from the image data 71, on the basis of the image cutting-out information 51 which has been acquired from the processor memory section 64S, and outputs the image data for display to the image expanding portion 82S.

The image expanding portion 82S reads out the magnification information 53 corresponding to the display area which has been selected or switched in the selecting section 200, from the processor memory section 64S, on the basis of the display area information that has been input from the processor CPU61. Then, the image expanding portion 82S electronically expands the image data for display, which has been input from the image cutting-out portion 81S, on the basis of the magnification information 53 that has been acquired from the processor memory section 64S, and outputs the image data for display to the mask processing portion 83S.

The mask processing portion 83S reads out the mask image data 86 corresponding to the display area which has been selected or switched in the selecting section 200, from the processor memory section 64S, on the basis of the display area information that has been input from the processor CPU 61. Then, the mask processing portion 83S subjects the image data for display, which has been input from the image expanding portion 82S, to a masking process, on the basis of the mask image data 86 that has been acquired from the processor memory section 64S, and outputs the image data for display, which has been subjected to the masking process, to the display driver 66. Thereby, the observation image of the site to be observed on the basis of the image data for display is displayed on the monitor 14.

Thus, the image cutting-out information 51, the magnification information 53 and the like which respectively correspond to the plurality of patterns of the display area, are previously stored, and thereby an adequate observation image which shows no vignetting is obtained, even when the display area has been selected or switched. As a result, a similar effect to the effect described in the above described embodiment is obtained.

[Example Applied to Capsule System]

The electronic endoscope which constitutes the endoscope apparatus of the present invention includes an elasticity endoscope, a rigid endoscope, an endoscope for industry and a capsule system (also referred to as capsule type endoscope). The electronic endoscope will be described in detail below with reference to drawings, while the capsule system is taken as an example.

Figure 17:
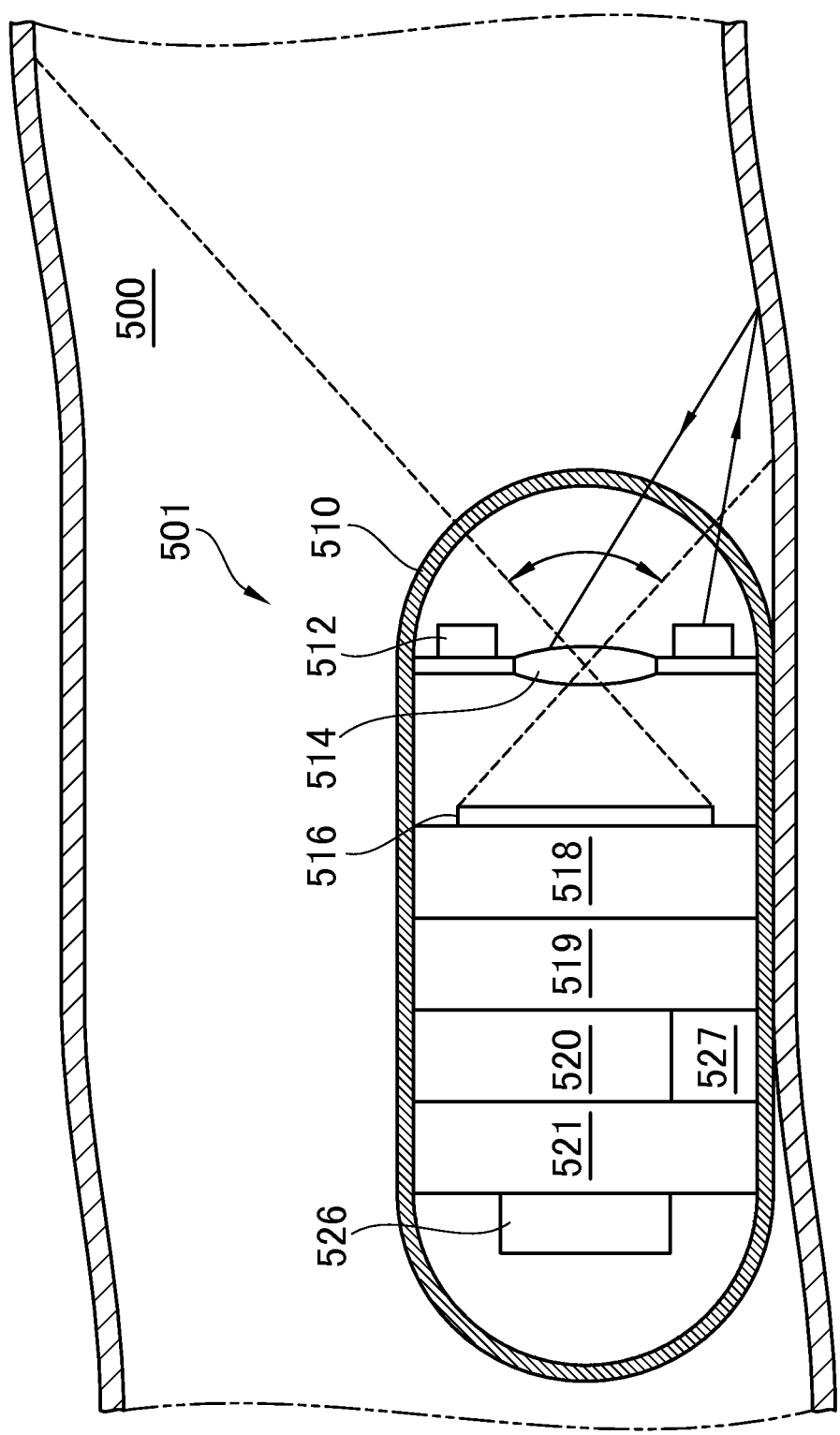
FIG. 17 is a schematic view of a capsule system which is used in the endoscope apparatus of the present invention.

As shown in FIG. 17, the capsule system 501 contains a lighting system 512, and a camera which is provided with an optical system 514 and an image sensor 516. The image which has been captured by the image sensor 516 is processed by an image processor 518. The image processor 518 can be implemented via a software which is carried out in a digital signal processing part (DSP) or a central processing unit (CPU), in a hardware, or in a combination of both the software and the hardware. The processed image is compressed by an image-compressing subsystem 519 (that is implemented sometimes in software which is carried out by DSP of image processor 518, depending on embodiment). The compressed data is stored in an archive memory system 520. The capsule system 501 contains a battery power source 521 and an output port 526. The capsule system 501 can advance in the alimentary tract (GI tract: gastrointestinal tract) 500 by peristaltic motion.

An LED can be also implemented in the lighting system 512. In FIG. 17, the LED is arranged adjacent to an opening of the camera, but can be also arranged in another place. A light source is occasionally arranged behind the opening, for instance. Another light source such as a laser diode is also used sometimes. A white light source or a combination of two or more light sources each having narrow wavelength band is also used sometimes, as another method. In order to emit light having a long wavelength, a white LED can be also used together with a phosphorescent material which is excited by the light of the LED. The white LED contains a blue LED or a purple LED sometimes. A predetermined portion of the capsule housing for passing light therethrough is made from a glass or a polymer, any of which is biologically compatible.

The optical system 514 is a system which corresponds to one form of the observation optical system of the present invention, and makes the image sensor 516 read the image of the wall of the lumen such as a GI tract 500, and may be a system which contains a plurality of refractive lens elements, diffractive lens elements, or reflective lens elements.

The image sensor 516 is a sensor which converts the intensity of received light into the corresponding electrical signal, and can be provided by a charge-coupled device (CCD) or a complementary metal oxide semiconductor (CMOS) type device. The image sensor 516 may react to a single color, or sometimes contains a color filter array which can capture a color image (for instance, by using RGB or CYM representation). This image sensor 516 corresponds to one form of the solid-state imaging element of the present invention.

It is preferable that an analog signal sent from the image sensor 516 be converted into a digital form so as to allow it to be processed in the digital form. Such a conversion is carried out with the use of an analog-to-digital (A/D) converter which is provided in the sensor (in case of present embodiment) or in another portion of the capsule housing 510. The A/D unit can be provided between the image sensor 516 and another portion of the system. The LED of the lighting system 512 is synchronized with an operation of the image sensor 516. As one of the functions in the control module (unillustrated) of the capsule system 501, there is a function of controlling the LED during a capture operation of the image.

An endoscope memory section 527 corresponds to one form of the memory section of the present invention, and stores the image cutting-out information 51 and the magnification information 53, which adapt to the attachment accuracy of the optical system 514 and the image sensor 516, similar to the endoscope memory section 49 of the above described embodiment. The image cutting-out information 51 and the magnification information 53 which are stored in the endoscope memory section 527 are transmitted to the processor device through the output port 526.

Figure 18:
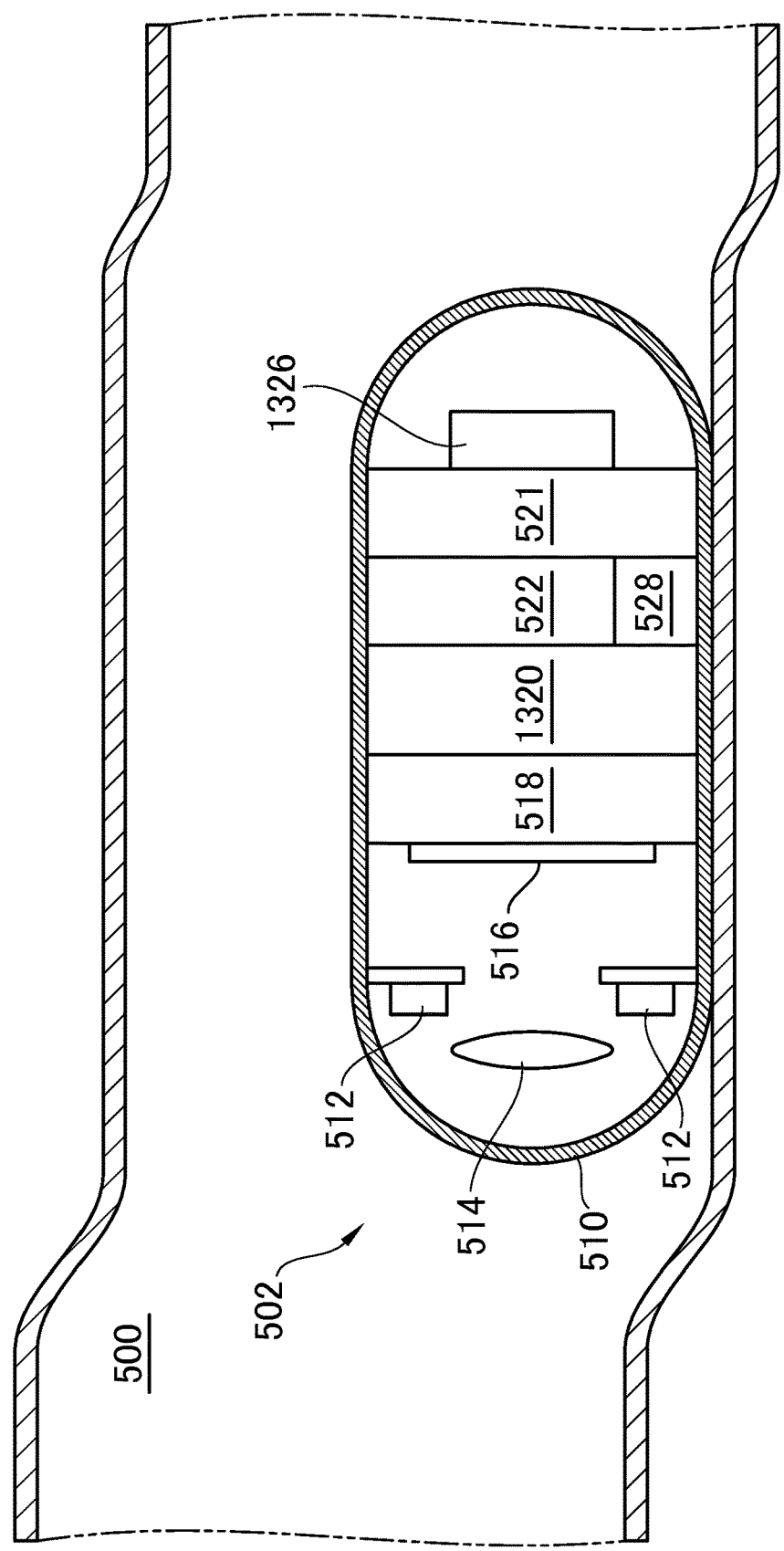
FIG. 18 is a schematic view of a capsule system in other embodiment.
Figure 19:
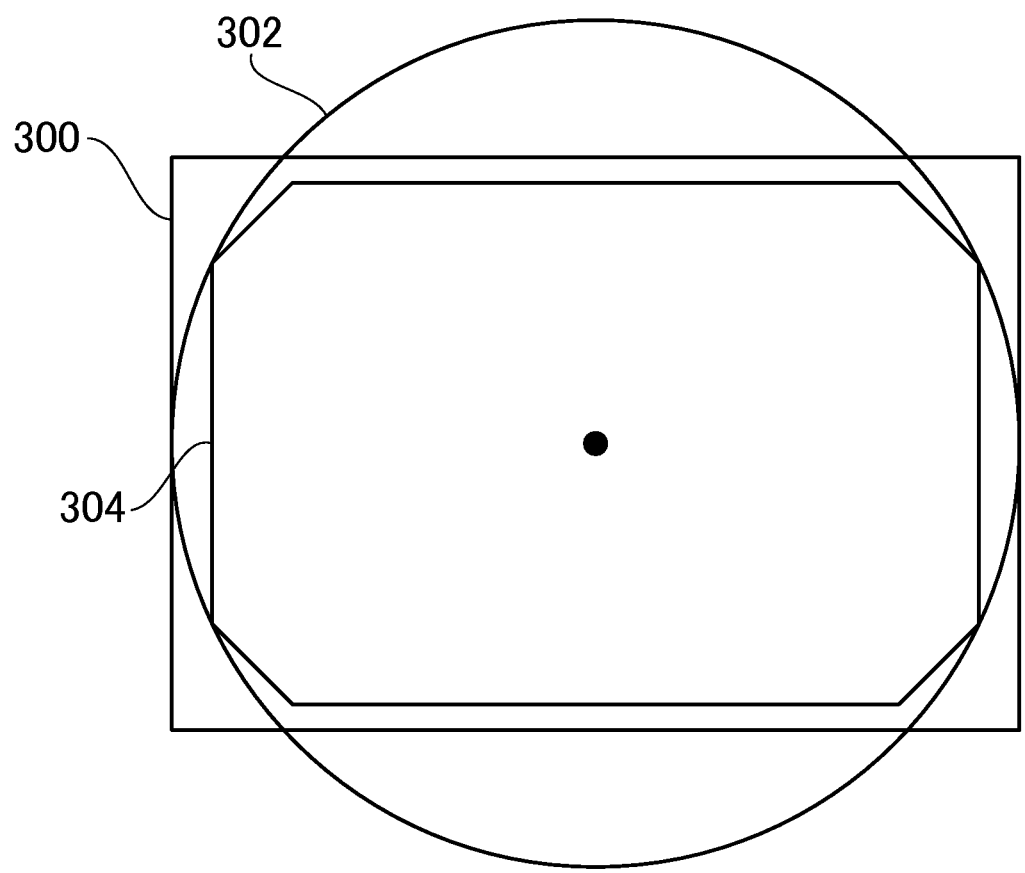
FIG. 19 is an explanatory view for describing a positional relationship among an effective pixel area, an imaging area and a display area, in a state in which the center of the effective pixel area matches with the center of the observation optical system.
Figure 20:
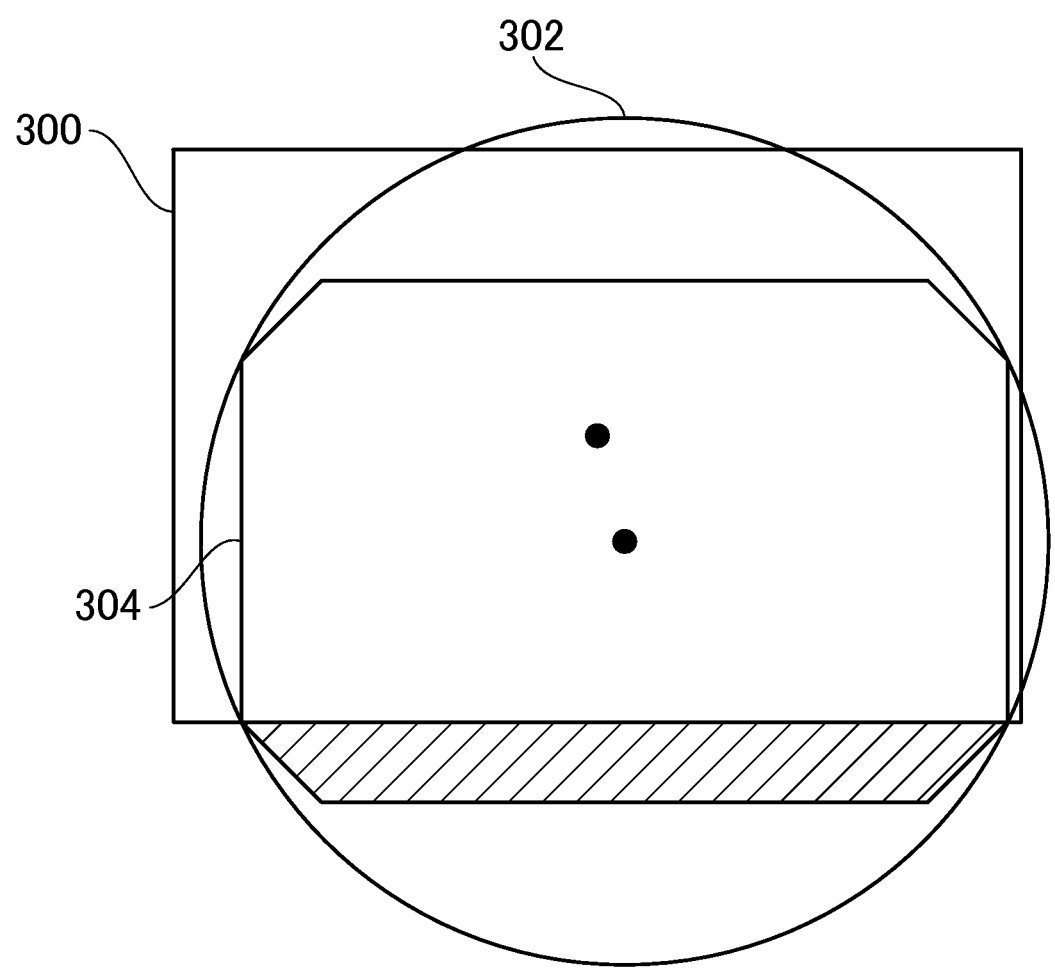
FIG. 20 is an explanatory view for describing a positional relationship among the effective pixel area (displayable pixel area), the imaging area and the display area, in a state in which deviation occurs between the center of the effective pixel area and the center of the observation optical system.

FIG. 18 shows a swallowing type capsule system 502 according to one embodiment of the present invention. The capsule system 502 can have substantially the same configuration as that of the capsule system 501 of FIG. 17, except the point that the archive memory system 520 and the output port 526 are not needed. The capsule system 502 contains also a communication protocol encoder 1320 and a transmitter 1326 which are used for wireless transmission. The same reference numerals are designated to substantially the same elements among the elements of the capsule system 501 and the capsule system 502. Accordingly, those structures and functions are not described again here. The control module 522 integrally controls the whole of the capsule system 502. The communication protocol encoder 1320 is implemented via a software which is carried out in DSP or CPU, in a hardware, or in a combination of the software and the hardware. The transmitter 1326 contains an antenna system for transmitting a captured digital image.

A part of a ROM (unillustrated) in the control module 522 functions as an endoscope memory section 528. The endoscope memory section 528 is a section corresponding to one form of the memory section of the present invention, and stores the image cutting-out information 51 and the magnification information 53 which adapt to the attachment accuracy of the optical system 514 and the image sensor 516, similar to the endoscope memory section 49 of the above described embodiment. The image cutting-out information 51 and the magnification information 53 which are stored in the endoscope memory section 528 are transmitted to the processor device through the transmitter 1326.

The processor device corresponding to the above described capsule system 501 and the capsule system 502 has basically the same configuration as that of the processor device of the above described embodiment, except the point that the processor device adapts to the capsule system; and conducts the image cutting-out process on the basis of the image cutting-out information 51, the image expanding process on the basis of the magnification information 53, and the like. Thereby, a similar effect to the effect described in the above described embodiment is obtained.

[Others]

In the above described embodiment, the processor CPU61 corresponding to the information acquiring section of the present invention acquires the image cutting-out information 51 and the magnification information 53 from the electronic endoscope 11, but may acquire the image cutting-out information 51 and the magnification information 53 which have been input in the unillustrated operating section of the processor device 13, or may acquire the image cutting-out information 51 and the magnification information 53 from a communication interface, a memory card or the like.

In addition, a plurality of types of image cutting-out information 51 and the magnification information 53 which correspond to a plurality of types of electronic endoscopes 11 may be previously stored in the processor memory section 64; and the image cutting-out information 51 and the magnification information 53 which correspond to the type of the electronic endoscope 11 may be selected, on the basis of the identification information of the electronic endoscope 11 and the like, which is input from the electronic endoscope 11 to the processor device 13.

In the above described embodiment, the light source device 12 and the processor device 13 are separately provided, but both may be integrally provided.

It goes without saying that the present invention is not limited to the above described embodiments, and can be modified in various ways in such a range as not to deviate from the concept of the invention.

What is claimed is:

1. An endoscope apparatus comprising:
   an observation optical system;
   a solid-state imaging element that is relatively positioned and fixed with respect to the observation optical system, obtains an optical image formed thereon by the observation optical system, and has a plurality of photoelectric conversion elements arrayed therein which photoelectrically convert the optical image;
   a memory section that stores image cutting-out information therein that specifies an image cutting-out region for a process of cutting out an image for display, which corresponds to a display area to be displayed on a monitor, from an image generated on the basis of an imaging signal of the solid-state imaging element;
   a processor configured to perform steps of:
      obtaining the image cutting-out region, from an overlapping region in which a displayable pixel area of the solid-state imaging element and an imaging area of the optical image to be formed on the solid-state imaging element by the observation optical system overlap one another, where the center of the imaging area is matched with the center of the display area;
      storing in the memory section the image cutting-out information based on the image cutting-out region;
      cutting out an image for display based on the cutting-out information stored in the memory section;
      expanding the image for display to an image size of the display area, when an image size of the cut-out image for display becomes smaller than the image size of the display area due to deviation between the center of the displayable pixel area and the center of the imaging area.

2. The endoscope apparatus according to claim 1, wherein the processor is configured to perform further steps of:
   storing magnification information calculated from the deviation between the center of the displayable pixel area and the center of the imaging area, and
   expanding the image for display according to the magnification information stored in the memory section.

3. The endoscope apparatus according to claim 2, wherein the memory section has the image cutting-out information and the magnification information corresponding to each of a plurality of the display areas stored therein, and is provided with a selecting section which selects the display area to be displayed on the monitor out of the plurality of display areas,
   the processor is configured to perform further steps of:
      acquiring the image cutting-out information and the magnification information corresponding to the display area which has been selected in the selecting section from the memory section, cutting out the image for display from the image on the basis of the image cutting-out information, and
expanding the image for display according to the magnification information.

4. The endoscope apparatus according to claim 1, wherein the image cutting-out information which is stored in the memory section is information which shows the image cutting-out region having the same aspect ratio as that of the display area.

5. The endoscope apparatus according to claim 1, wherein the processor is configured to perform further steps of:
expanding the image for display, when the image cutting-out information is information that shows the image cutting-out region in which at least either of the following Expression (1) and Expression (2) is satisfied $$V-L_V \leq D_V \quad (1)$$

$$H-L_H \leq D_H \quad (2)$$

in the case where the numbers of pixels in a vertical direction and a horizontal direction in the displayable pixel area are represented by 2V and 2H, the numbers of pixels in a vertical direction and a horizontal direction in the display area are represented by 2LV and 2LH, and amounts of deviation between the center of the displayable pixel area and the center of the imaging area in a vertical direction and a horizontal direction in terms of the numbers of pixels are represented by DV and DH.

6. The endoscope apparatus according to claim 5, wherein the processor is configured to perform further step of:
expanding the image for display at a higher magnification out of the magnifications m expressed by the following Expression (3) and Expression (4), respectively $$m=L_V/(V-D_V) \quad (3)$$

$$m=L_H/(H-D_H) \quad (4)$$

when magnification in which the image for display is expanded is represented by m.

7. The endoscope apparatus according to claim 6, wherein the processor is configured to perform further step of:
expanding the image for display when the higher magnification is admissible magnification or less.

8. The endoscope apparatus according to claim 1, wherein the processor is configured to perform further step of:
masking the image for display so that it becomes the same shape as that of the display area.

9. The endoscope apparatus according to claim 7, wherein the admissible magnification equals 2.

* * * * *